US010639415B2

(12) United States Patent
Yi

(10) Patent No.: US 10,639,415 B2
(45) Date of Patent: May 5, 2020

(54) MEDICAL IMAGING APPARATUS AND CONTROLLING METHOD THEREOF

(71) Applicant: SAMSUNG ELECTRONICS CO., LTD., Suwon-si (KR)

(72) Inventor: Jong Hyon Yi, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 1037 days.

(21) Appl. No.: 14/749,926

(22) Filed: Jun. 25, 2015

(65) Prior Publication Data
US 2016/0067402 A1 Mar. 10, 2016

(30) Foreign Application Priority Data

Sep. 4, 2014 (KR) ........................ 10-2014-0117544

(51) Int. Cl.
*A61B 6/00* (2006.01)
*A61M 5/00* (2006.01)
*A61B 90/00* (2016.01)

(52) U.S. Cl.
CPC ....... *A61M 5/007* (2013.01); *A61B 2090/374* (2016.02); *A61B 2090/378* (2016.02); *A61B 2090/3762* (2016.02)

(58) Field of Classification Search
CPC ............................... A61M 5/007; A61B 5/077
See application file for complete search history.

(56) References Cited

U.S. PATENT DOCUMENTS

| 6,195,579 B1* | 2/2001 | Carroll ................. G01R 33/561 324/306 |
| 6,246,782 B1* | 6/2001 | Shapiro ................. G06T 7/0012 128/925 |
| 6,337,992 B1 | 1/2002 | Gelman |
| 6,397,097 B1 | 5/2002 | Requardt |

(Continued)

FOREIGN PATENT DOCUMENTS

| JP | 2008-264274 A | 11/2008 |
| KR | 10-2010-0010742 A | 2/2010 |

OTHER PUBLICATIONS

Zheng et al (Three-dimensional gadolinium-enhanced coronary magnetic resonance angiography: Initial experience).*

(Continued)

*Primary Examiner* — Joel F Brutus
(74) *Attorney, Agent, or Firm* — Sughrue Mion, PLLC

(57) ABSTRACT

Disclosed herein are a medical imaging apparatus including a scanner configured to scan an object, an image generator configured to generate a monitoring image to monitor variations in brightness of a region of interest (ROI) of the object, a controller configured to determine a peak of brightness in the monitoring image, and a user interface configured to display the monitoring image and an indicator of the determined peak, and a method of controlling the same. According to the medical imaging apparatus and the method of controlling the same, over-injection of a contrast agent into the object may be prevented while a medical image is acquired, and an image may be obtained when the contrast agent is in an optimum state in consideration of various environmental factors. Accordingly, lesions and diseases may be more accurately determined and interpreted by using the medical image.

25 Claims, 23 Drawing Sheets

(56) References Cited

U.S. PATENT DOCUMENTS

| | | |
|---|---|---|
| 6,408,201 B1 | 6/2002 | Foo et al. |
| 6,425,864 B1 | 7/2002 | Foo et al. |
| 2002/0091316 A1 | 7/2002 | Foo et al. |
| 2004/0061496 A1* | 4/2004 | Ookawa ............... G01R 33/563 324/307 |
| 2005/0089137 A1* | 4/2005 | Toth ....................... A61B 6/032 378/19 |
| 2006/0239917 A1 | 10/2006 | Klotz et al. |
| 2008/0119715 A1 | 5/2008 | Gonzalez Molezzi et al. |
| 2008/0262354 A1* | 10/2008 | Yoshida ................. A61B 8/469 600/443 |
| 2009/0094058 A1 | 4/2009 | Reiner |
| 2009/0225083 A1* | 9/2009 | Thomas ................. G01R 13/02 345/440 |
| 2010/0245389 A1* | 9/2010 | Aoki .................. G01R 13/0245 345/641 |
| 2010/0262007 A1* | 10/2010 | Medlin .................... A61B 8/14 600/446 |
| 2013/0041257 A1 | 2/2013 | Nemoto |
| 2013/0169782 A1* | 7/2013 | Choi .................... A61B 5/0077 348/77 |

OTHER PUBLICATIONS

Bae (Intravenous contrast medium administration and scan timing at CT: considerations and approaches).*

Communication from the Korean Intellectual Property Office dated Apr. 21, 2016 in a counterpart Korean application No. 10-2014-0117544.

Communication dated Aug. 25, 2015 issued by the Korean Intellectual Property Office in counterpart Korean Patent Application No. 10-2014-0117544.

Takayoshi Yamaguchi, et al., "Development of Test Bolus Tracking Method and Usefulness in Coronary CT Angiography", Radiological Center, Hokkaido Social Insurance Hospital, Received Mar. 19, 2009, Revision accepted Jun. 16, 2009, pp. 1032-1040.

* cited by examiner

MEDICAL IMAGING APPARATUS AND CONTROLLING METHOD THEREOF

CROSS-REFERENCE TO RELATED APPLICATION(S)

This application claims priority from Korean Patent Application No. 10-2014-0117544, filed on Sep. 4, 2014 in the Korean Intellectual Property Office, the disclosure of which is incorporated herein by reference in its entirety.

BACKGROUND

1. Field

Exemplary embodiments relate to medical imaging apparatuses acquiring an image of the inside of an object and methods of controlling the same.

2. Description of the Related Art

As interest in health increases, research on medical imaging apparatuses has been vigorously performed. The medical imaging apparatuses include ultrasound imaging apparatuses, X-ray imaging apparatuses, magnetic resonance imaging (MRI) apparatuses, positron emission tomography (PET) apparatuses, and the like.

X-ray imaging apparatuses obtain an image of the inner structure of an object by irradiating the object with X-rays, and analyzing X-rays that propagate through the object. Since X-ray transmission is variable for each tissue of the object, the inner structure of the object can be imaged by variation of an intensity of X-rays that have propagated through the object.

MRI apparatuses acquire an image of an inner portion of an object by converting energy, which is emitted from atomic nuclei by supplying a constant frequency and energy while a constant magnetic field is applied to hydrogen atomic nuclei of the object, into a signal. The MRI apparatuses hold a very important position in diagnosis using medical images due to relatively easy image capturing conditions, excellent contrast in soft tissue, and ability to provide various diagnosis information images thereof.

Ultrasound imaging apparatuses generate an image of the inside of an object, such as, for example, a soft tissue tomogram or a blood stream tomogram, by emitting ultrasound energy toward a target region from the surface of the object and receiving reflected ultrasound energy. The ultrasound imaging apparatuses are relatively small, inexpensive, non-invasive, and nondestructive, as compared to other diagnostic imaging apparatuses, such as X-ray diagnosis apparatuses, magnetic resonance imaging (MRI) apparatuses, and nuclear medicine diagnosis apparatuses.

Meanwhile, interventions and angiography using a contrast agent have been applied to X-ray imaging and MRI, and Contrast Enhanced Ultrasound (CEUS) has been applied to detection of lesions and to diagnosis of diseases.

SUMMARY

Therefore, it is an aspect of one or more exemplary embodiments to provide a medical imaging apparatus to obtain an image the inside of an object into which a contrast agent is injected and a method of controlling the same.

Additional aspects of the exemplary embodiments will be set forth in part in the description which follows and, in part, will be apparent from the description, or may be learned by practice of the exemplary embodiments.

In accordance with one aspect of one or more exemplary embodiments, a medical imaging apparatus includes a scanner configured to scan an object, an image generator configured to generate a monitoring image to monitor at least one variation in a brightness of a region of interest (ROI) of the object, a controller configured to determine a peak of the brightness in the monitoring image, and a user interface configured to display the monitoring image and an indicator of the determined peak.

The scanner may be further configured to scan the ROI.

The image generator may be further configured to generate an ROI image based on a result of the scanning the ROI.

The user interface may be further configured to display the indicator on the monitoring image.

The scanner may be fixed at a peripheral position of the ROI and be further configured to scan the ROI at least twice at predetermined time intervals.

The monitoring image may include an image that shows a graph that depicts at least one variation in the brightness of the ROI image as a function of time.

The user interface may be further configured to receive, from a user, a confirmation of a position of the indicator.

The user interface may be further configured to receive, from the user, a position change command that relates to changing the position of the indicator.

The user interface may be further configured to display the indicator based on the changed position that results from the received position change command.

The scanner may be further configured to scan an area of a diagnosis of the object.

The area of the diagnosis may be different from the ROI.

The scanner may be further configured to scan the ROI in correspondence with an injection of a test contrast agent and to scan the area of the diagnosis in correspondence with an injection of a main contrast agent.

An injection amount of the test contrast agent may be smaller than an injection amount of the main contrast agent.

The injection of the test contrast agent may occur before the injection of the main contrast agent.

The controller may be further configured to calculate a first arrival time period during which the brightness reaches the peak after the injection of the test contrast agent based on the position of the indicator.

The medical imaging apparatus may further include a storage configured to store a second arrival time period during which at least one from among the test contrast agent and the main contrast agent arrives at the area of the diagnosis.

The controller may be further configured to calculate a starting time of the scanning of the area of the diagnosis based on the first arrival time period and the second arrival time period.

The controller may be further configured to calculate a starting time of the scanning of the area of the diagnosis by adding the first arrival time period and the second arrival time period to a time of occurrence of the injection of the main contrast agent.

The user interface may be further configured to receive, from the user, information that indicates at least one from among the ROI and the area of the diagnosis.

The scanner may be further configured to perform scout scanning on the object that is usable by the image generator for generating a scout image.

The user interface may be further configured to display the scout image, and the ROI may be set on the displayed scout image.

The scanner may be further configured to scan the area of the diagnosis at least twice at predetermined time intervals while rotating around the area of the diagnosis.

The image generator may be further configured to generate a diagnostic image in accordance with the scanning the area of the diagnosis, and the user interface may be further configured to display the generated diagnostic image.

The medical imaging apparatus may further include a voice output device configured to output a guidance message that includes information relating to instructing the object to hold his or her breath before the scanning the area of the diagnosis is initiated.

In accordance with another aspect of one or more exemplary embodiments, a method for controlling a medical imaging apparatus includes scanning an object, generating a monitoring image configured to monitor at least one variation in a brightness in a region of interest (ROI) of the object, determining a peak of the brightness in the monitoring image, and displaying the monitoring image and an indicator of the determined peak.

The scanning the object may include scanning the ROI.

The generating the monitoring image may include generating an ROI image based on a result of the scanning the ROI, and the monitoring image may include an image which is usable for monitoring the at least one variation in the brightness of the ROI image.

The method may further include receiving, from a user, a confirmation of a position of the indicator.

The method may further include scanning an area of a diagnosis of the object.

The scanning the ROI may include scanning the ROI in correspondence with an injection of a test contrast agent, and the scanning the area of the diagnosis may include scanning the area of the diagnosis in correspondence with an injection of a main contrast agent.

The method may further include calculating a first arrival time period during which the brightness reaches the peak after the injection of the test contrast agent based on the position of the indicator.

The method may further include calculating a starting time of the scanning of the area of the diagnosis based on the first arrival time period and a second arrival time period during which at least one from among the test contrast agent and the main contrast agent arrives at the area of the diagnosis.

The scanning the area of diagnosis of the object may include outputting a guidance message that includes information relating to instructing the object to hold his or her breath before the scanning the area of the diagnosis is initiated.

According to the medical imaging apparatus and the method for controlling the same, over-injection of the contrast agent into the object may be prevented while a medical image is acquired by injecting the contrast agent into the object. In addition, an image may be obtained when the contrast agent is in an optimum state, since various environmental factors such as types of the contrast agent, injection protocols, change of the object, or parts of the object to be scanned are considered. Accordingly, lesions and diseases may be more accurately determined and interpreted by using the medical image.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
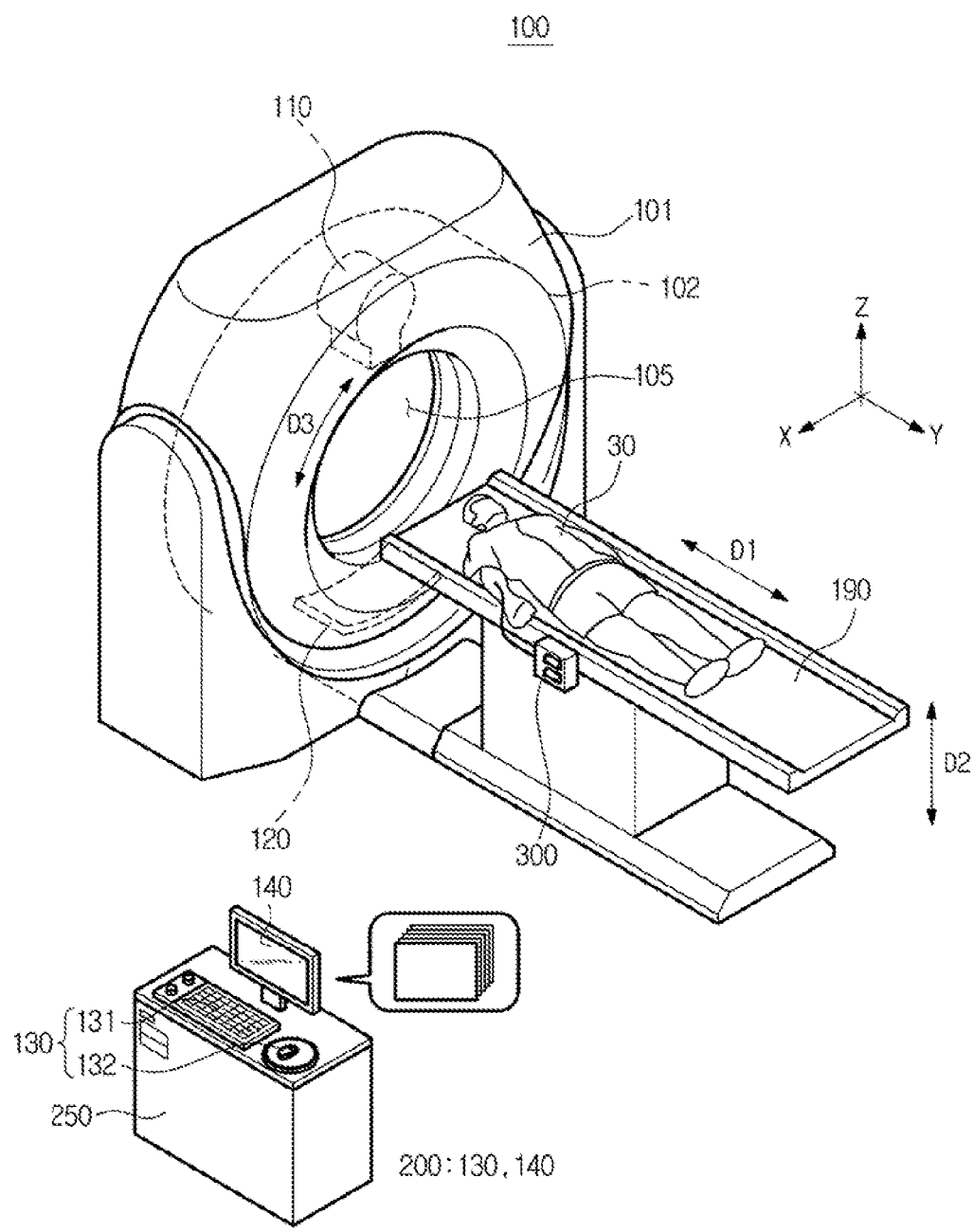
FIG. 1 is a perspective view illustrating an appearance of a medical imaging apparatus, according to an exemplary embodiment.

Reference will now be made in detail to exemplary embodiments, examples of which are illustrated in the accompanying drawings, wherein like reference numerals refer to like elements throughout.

Hereinafter, a medical imaging apparatus and a method for controlling the medical imaging apparatus will be described.

As used herein, the medical imaging apparatus refers to an imaging apparatus using a contrast agent such as ultrasound imaging apparatuses, X-ray imaging apparatuses, and magnetic resonance imaging (MRI) apparatuses. In particular, the medical imaging apparatus may be an imaging apparatus requiring a scout scan or pre-shot such as computed tomography (CT) scanners, from among the X-ray imaging apparatuses or MRI apparatuses. Hereinafter, a CT scanner will be described as an example of the medical imaging apparatus for descriptive convenience.

FIG. 1 is a perspective view illustrating an appearance of a medical imaging apparatus 100, according to an exemplary embodiment.

Referring to FIG. 1, the medical imaging apparatus 100 includes a housing 101 for X-ray irradiation and detection, a table 190 configured to move an object, and a main body 250 configured to control an operation of the medical imaging apparatus 100.

A cylindrical gantry 102 is installed in the housing 101. In the gantry 102, an X-ray source 100 that emits X-rays and an X-ray detector 120 that detects X-rays are disposed to face each other. The X-ray source 110 is a device that generates X-rays and emits the X-rays toward an object 30, and may be implemented as an X-ray source assembly provided with a filtering unit (also referred to herein as a "filter") that filters the emitted X-rays. In this regard, the object 30 may be living bodies such as humans and animals or living tissues such as blood vessels, bones, and muscles, without being limited thereto, and any object for which an inner structure thereof may be imaged by the medical imaging apparatus 100 may also be used as the object 30.

The X-ray detector 120 is a device that detects X-rays that have propagated through the object 30, and may be disposed at an opposite side of the X-ray source 100. As the table 190 moves, the object 30 may be disposed between the X-ray source 110 and the X-ray detector 120, and X-rays that have emitted from the X-ray source 110 have propagated through the object 30 are detected by the X-ray detector 120.

The gantry 102 rotates around a bore 105 by an angle of between 180 degrees and 360 degrees. As the gantry 102 rotates, the X-ray source 110 and the X-ray detector 120 rotate. This will be described in more detail below with reference to FIG. 3.

The table 190 moves the object 30 subject to X-ray imaging into the bore 105. The table 190 moves in a y-axial direction and a z-axial direction while maintaining horizontality relative to the ground. In this regard, the moving direction of the table 190 along the y-axial direction is referred to as a D1 direction, and the moving direction of the table 190 along the z-axial direction is referred to as a D2 direction. The table 190 may locate an area of a diagnosis between the X-ray source 110 and the X-ray detector 120 while moving in the D1 and D2 directions. The table 190 may be fixed not to move in an x-axial direction, or may be disposed to be movable in the x-axial direction in order to adjust a lateral spacing within the bore 105.

The table 190 may be provided with a medical injector 300 at one side, and the medical injector 300, which is filled with a contrast agent, is connected to the object 30 such that the contrast agent is injected into the object 30. The medical injector 300 may be detachably mounted on one side of the table 190. In addition, alternatively with respect to FIG. 1, the medical injector 300 may be mounted on a separate movable support (not shown) instead of being mounted on one side of the table 190 and move in accordance with movement of the support. The medical injector 300 will be described in more detail below with reference to FIG. 4.

The main body 250 may accommodate major constituent elements, e.g., a controller (400 of FIG. 5), of the medical imaging apparatus 100. The controller 400 may be configured to generate various control signals to control operation of the medical imaging apparatus 100, such as rotation of the gantry 102 or movement of the table 190, and/or to control an amount of X-rays emitted from the X-ray source 110, which will be described in more detail below.

A user interface 200 for user's manipulation may be mounted on the main body 250. The user interface 200 may receive an instruction or command to control operation of the medical imaging apparatus 100 from a user, and may provide various screens related to the operation of the medical imaging apparatus 100. In particular, the user refers to a medical professional to perform diagnosis of an object by using the medical imaging apparatus 100, such as a doctor, a medical radiation technologist, and a nurse, without being limited thereto. The user may also include any person using the medical imaging apparatus 100.

The user interface 200 may include a keyboard 131 and/or a mouse 132 for a user's input. The user interface 200 may further include any one or more of a hardware input device such as a trackball, a foot switch, and a foot pedal, in addition to the keyboard 131 and the mouse 132. The user interface 200 may be mounted on the main body 250, as illustrated in FIG. 1. However, in case of the foot switch and the foot pedal, the user interface 200 may be disposed at a lower portion of the main body 250.

The user interface 200 may include a graphical user interface such as a touch pad, i.e., a software input device, for receiving the user's input. In case of the software input device, the user interface 200 may be displayed through a display apparatus 140 which will be described below.

As described above, the user interface 200 may include a variety of input devices 130, and the user may input any of a command to initiate X-ray scanning, a command to select types of scanning, a command to set a region of interest (ROI), a command to select an area of diagnosis, a command to select a time of injecting a contrast agent, and a command to select a peak brightness of the contrast agent through the user interface 200. The command input through the user interface 200 may be transmitted to the main body 250 via a wired or wireless communication network.

The user interface 200 may include a display apparatus 140 to provide various screens for operation of the medical imaging apparatus 100. The user interface 200 may include a display apparatus 140 such as a cathode ray tube (CRT), a liquid crystal display (LCD), and an organic light emitting diode (LED) display apparatus, without being limited thereto.

The display apparatus 140 of the user interface 200 may be integrated with a touch pad into which a manipulation command is input from the user, such as a touch screen panel (TSP).

The user interface 200 may display screens related to operation information of the medical imaging apparatus 100, such as any one or more of a screen to set the ROI, a screen to select the area of diagnosis, a screen to select the time of injecting the contrast agent, and a screen to select the peak brightness of the contrast agent and may display X-ray images acquired by X-ray scanning via the display apparatus 140 and implemented in any of various shapes.

The X-ray images acquired by X-ray scanning may include any of a single cross-sectional image, a plurality of cross-sectional images, or a three-dimensional (3D) image or a 3D stereo image generated based on the plurality of cross-sectional images in accordance with types of scanning. In this regard, the 3D image refers to an image acquired via volume rendering of 3D volume data generated based on the plurality of cross-sectional images with respect to a predetermined view point. In particular, the 3D image refers to a projected image obtained by projecting volume data onto a two-dimensional (2D) plane with respect to a predetermined view point. A 3D stereo image refers to an image generated by acquiring a left image and a right image by performing volume rendering on volume data at two viewpoints that respectively correspond to left and right eyes of a human, and combining the left and right images.

The user interface 200 may include a plurality of display apparatuses 140, as an alternative exemplary embodiment with respect to FIG. 1, thereby displaying different types of screens. For example, the user interface 200 may include a first display apparatus on which a cross-sectional image is displayed and a second display apparatus on which a 3D image or a 3D stereo image is displayed. Alternatively, a screen related to operation information of the medical imaging apparatus 100 may be displayed on the first display apparatus, and X-ray images acquired by X-ray scanning may be displayed on the second display apparatus.

Although the medical imaging apparatus 100 including the housing 101 and the cylindrical gantry 102 (hereinafter, referred to as a gantry-type medical imaging apparatus) is described above, the medical imaging apparatus 100 may also have any other shape that is different from that illustrated in FIG. 1.

Figure 2:
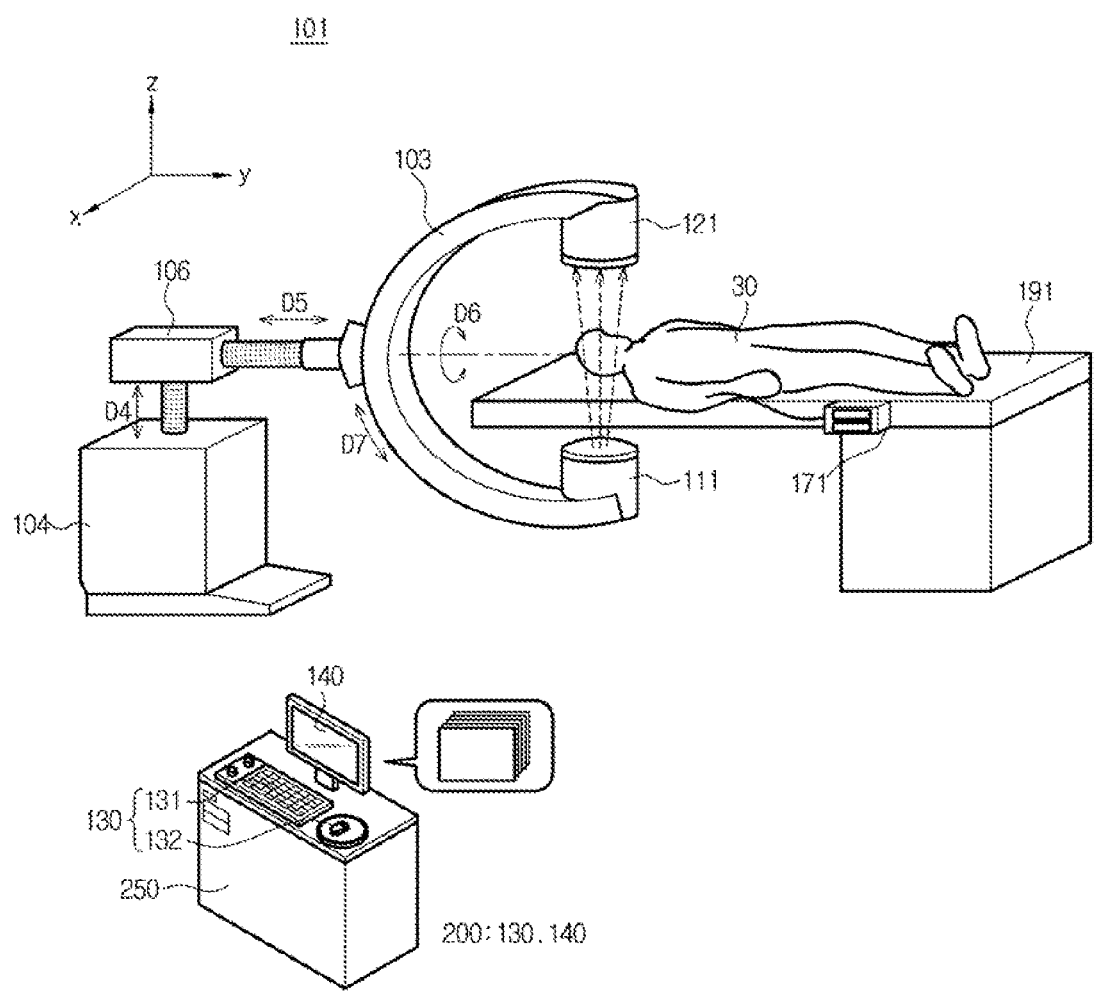
FIG. 2 is a perspective view illustrating an appearance of a medical imaging apparatus, according to another exemplary embodiment.

FIG. 2 is a perspective view illustrating an appearance of a medical imaging apparatus 101, according to another exemplary embodiment.

The medical imaging apparatus 101 may have a C-shaped arm structure (C-arm 103) as illustrated in FIG. 2. An X-ray source 111 that emits X-rays and an X-ray detector 121 that detects X-rays may be disposed at both ends of the C-arm 103 to face each other. As described above, the X-ray source 111 may be implemented as an X-ray source assembly provided with a filtering unit that filters the emitted X-rays.

The C-arm 103 may be connected to a support 104 via a connection shaft 106 and may move in a y-axial direction and a z-axial direction as the connection shaft 106 moves. In this regard, the moving direction of the C-arm 103 along the z-axial direction may be referred to as a D4 direction, and the moving direction of the C-arm 103 along the y-axial direction may be referred to as a D5 direction. The C-arm 103 may locate an area of a diagnosis between the X-ray source 111 and the X-ray detector 121 while moving in the D4 and D5 directions.

In addition, the C-arm 103 may be rotatable about an axis that corresponds to the D5 direction and rotatable in an orbital direction. In this regard, a rotation direction of the C-arm 103 about the D5 direction may be referred to as a D6 direction, and a rotation direction of the C-arm 103 along the orbital direction may be referred to as a D7 direction. As the C-arm 103 rotates in the D6 direction or D7 direction by an angle of between 180 degrees and 360 degrees, the X-ray source 111 and the X-ray detector 121 located at both ends of the C-arm 103 may also be rotated.

A table 191 on which the object 30 is located may move in the y-axial direction and the z-axial direction while maintaining horizontality relative to the ground. The table 190 may also move in an x-axial direction in addition to the y-axial and z-axial directions and may also rotate about the x-axial direction. Even when the C-arm 103 does not move, the area of diagnosis of the object 30 may be disposed between the X-ray source 111 and the X-ray detector 121 in accordance with the movement of the table 191. As the table 191 rotates about the x-axial direction, the rotational direction of the C-arm 103 may be determined or changed. For example, when the table 191 is located parallel to the y-axis as illustrated in FIG. 2, the C-arm 103 may perform X-ray scanning while rotating in the D6 direction. In addition, when the table 191 is located parallel to the x-axis in an alternative exemplary embodiment with respect to FIG. 2, the C-arm 103 may perform X-ray scanning while rotating in the D7 direction.

The table 191 may be provided with a medical injector 171 at one side, and the medical injector 171 may be detachably mounted on the table 191. In addition, the medical injector 171 may be mounted on a separate movable support (not shown) instead of being mounted on one side of the table 191.

The C-arm type medical imaging apparatus 101 may include a main body 250 and a user interface 200 disposed on the main body 250 in the same manner as in the gantry type medical imaging apparatus 100. The main body 250 and the user interface 200 are the same as those described above with reference to FIG. 1.

The medical imaging apparatus may be implemented as the gantry type as illustrated in FIG. 1 or as the C-arm type as illustrated in FIG. 2. Hereinafter, however, the gantry type medical imaging apparatus 100 will be described as an example of the medical imaging apparatus for descriptive convenience.

Figure 3A:
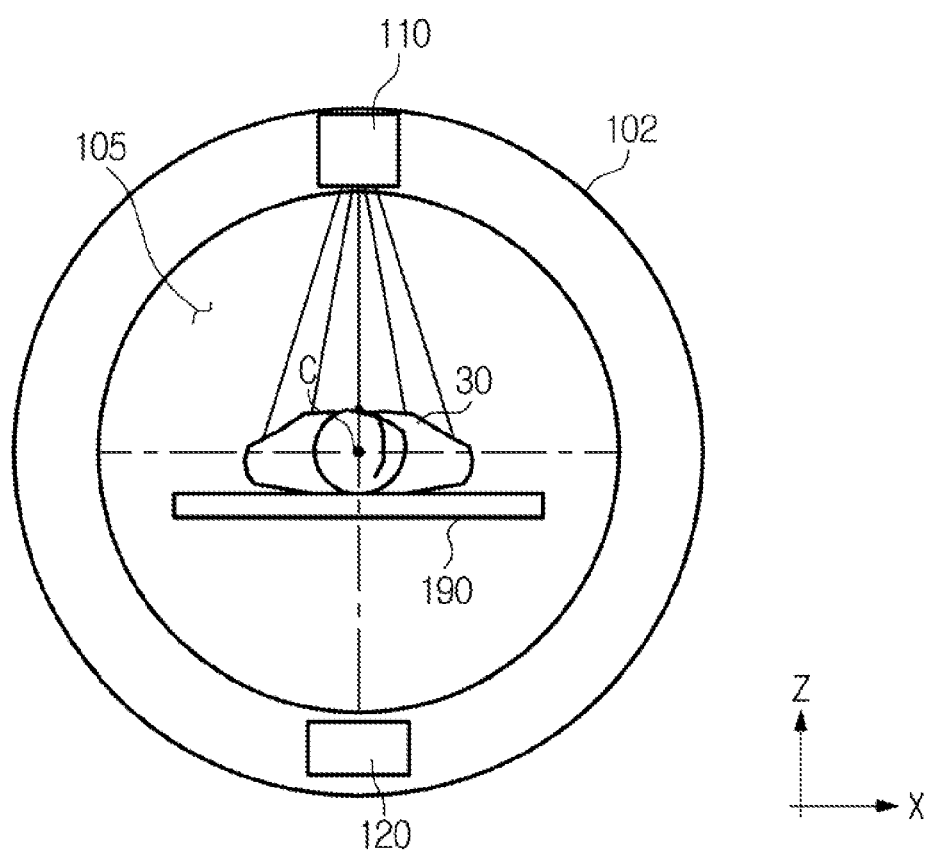
FIGS. 3A and 3B are diagrams illustrating a rotation of a gantry for scanning an area of diagnosis.
Figure 3B:
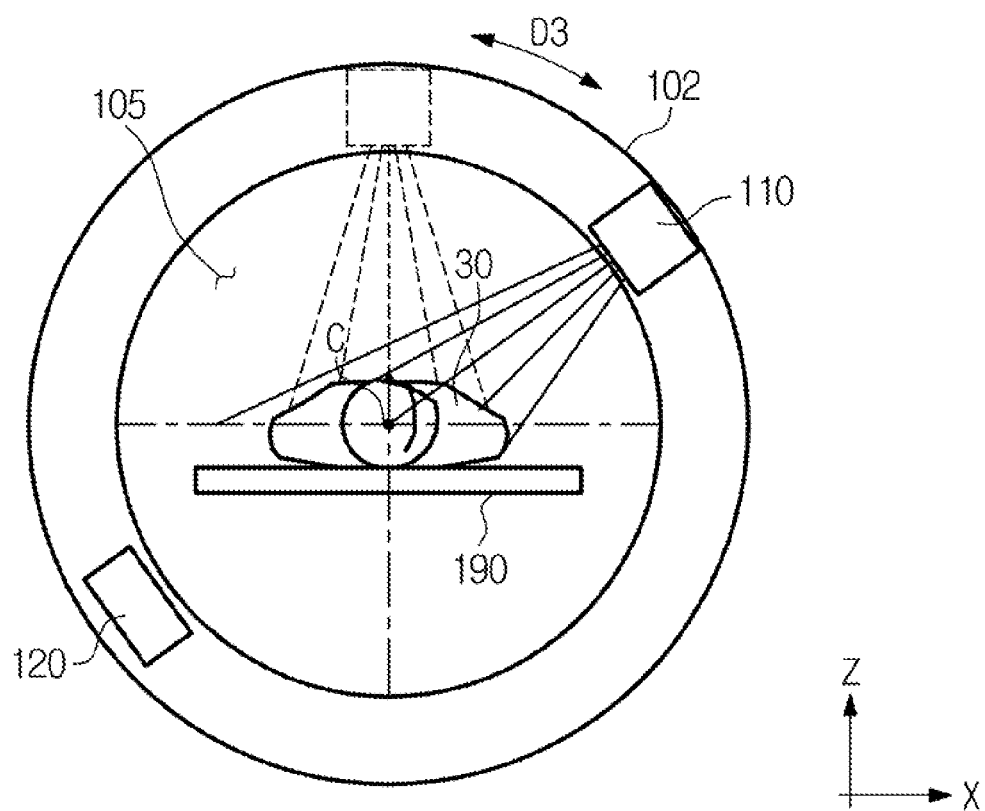

FIGS. 3A and 3B are diagrams illustrating a rotation of a gantry for scanning an area of a diagnosis.

Referring to FIGS. 3A and 3B, the table 190 of the medical imaging apparatus 100 may move into the bore 105 after a lateral position or a vertical position thereof is adjusted such that the center of the object 30 corresponds to the center C of the bore 105. Alternatively, the table 190 of the medical imaging apparatus 100 may move into the bore 105, and then the lateral or vertical position of the table 190 may be adjusted such that the center of the object 30 corresponds to the center C of the bore 105.

The medical imaging apparatus 100 rotates the gantry 102 in the D3 direction in order to acquire X-ray images of the area of a diagnosis of the object 30. While the gantry 102 rotates in the D3 direction, the X-ray source 110 emits X-rays toward the object 30 at predetermined periods or at predetermined time intervals, and the X-ray detector 120 detects X-rays that have propagated through the object 30. The X-ray source 110 may initiate emission of X-rays at a starting point above the object 30 as illustrated in FIG. 3A and rotate in the right hand direction of the object 30 by 360°, as illustrated in FIG. 3B in accordance with the rotation of the gantry 102. The X-ray source 110 emits X-rays a plurality of number of times (i.e., at least twice) until the X-ray source 110 returns to the starting point, thereby acquiring X-ray images of the area of the diagnosis.

Only when a main contrast agent is injected, x-ray scanning may be performed while the gantry 102 rotates. When a test contrast agent is injected, x-ray scanning is performed in a state where the gantry 102 is fixed. Before the injection of the contrast agent, x-ray scanning may be performed only in the state where the gantry 102 is fixed or in both states where the gantry 102 is rotated and fixed. This will be described in more detail below.

Figure 4:
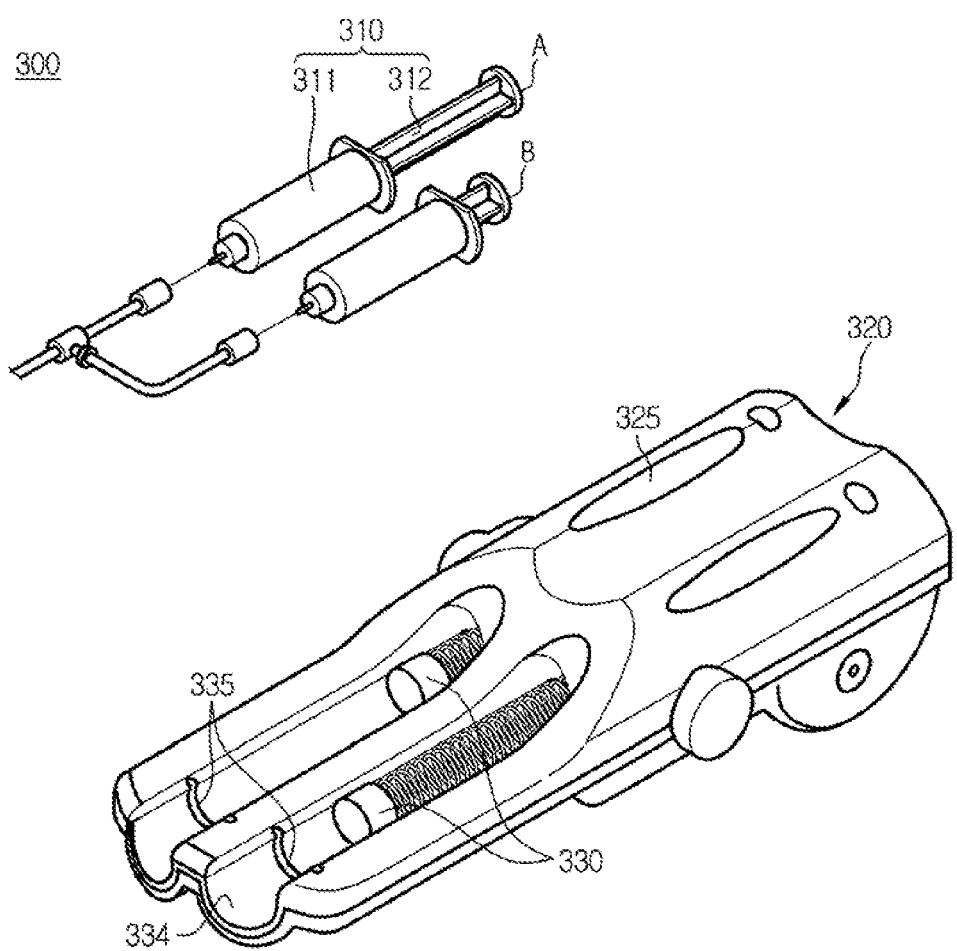
FIG. 4 is a diagram illustrating an appearance of a medical injector.

The test contrast agent or the main contrast agent is automatically injected into the object 30 in response to a user's injection command which is received via the user interface 200, and the medical injector 300 for injection of the contrast agent is as illustrated in FIG. 4.

FIG. 4 is a diagram illustrating an appearance of a medical injector 300.

The medical injector 300 may include a syringe 310 and an injection head 320 in which the syringe 310 is installed. The syringe 310 may include at least one syringe. When there are two syringes as illustrated in FIG. 4, the syringes may include a first syringe A filled with a contrast agent and a second syringe B filled with physiological saline. The syringe 310 may include a cylindrical cylinder 311 and a piston 312 configured to reciprocate within the cylinder 311, and the shape of the syringe 310 is not limited to that illustrated in FIG. 4.

A plurality of buttons 325 configured to manipulate an operation of the injection head 320 may be disposed on the top surface of the injection head 320. The injection head 320 includes a syringe support 334 to support the mounted syringe 310 and a fixing unit (also referred to herein as a "fixer") 335 to fix the syringe 310 disposed at one end of the support 334. The injection head 320 may include a piston driving unit (also referred to herein as a "piston driver") 330 to drive the piston 312 such that the piston 312 slides into the cylinder 311 or slides out of the cylinder 311.

The injection head 320 is connected to the main body 250 via a wired or wireless communication network, and receives a user's injection command from the main body 250, thereby driving the piston driving unit 330. The object 30 connected to one end of the syringe 310 receives the contrast agent or physiological saline in accordance with an operation of the piston driving unit 330.

The appearance of the medical imaging apparatus 100 provided with the medical injector 300 is described above. Hereinafter, the medical imaging apparatus 100 will be described in detail with reference to a control block diagram to control a time of injecting the contrast agent and a time of X-ray scanning.

Figure 5:
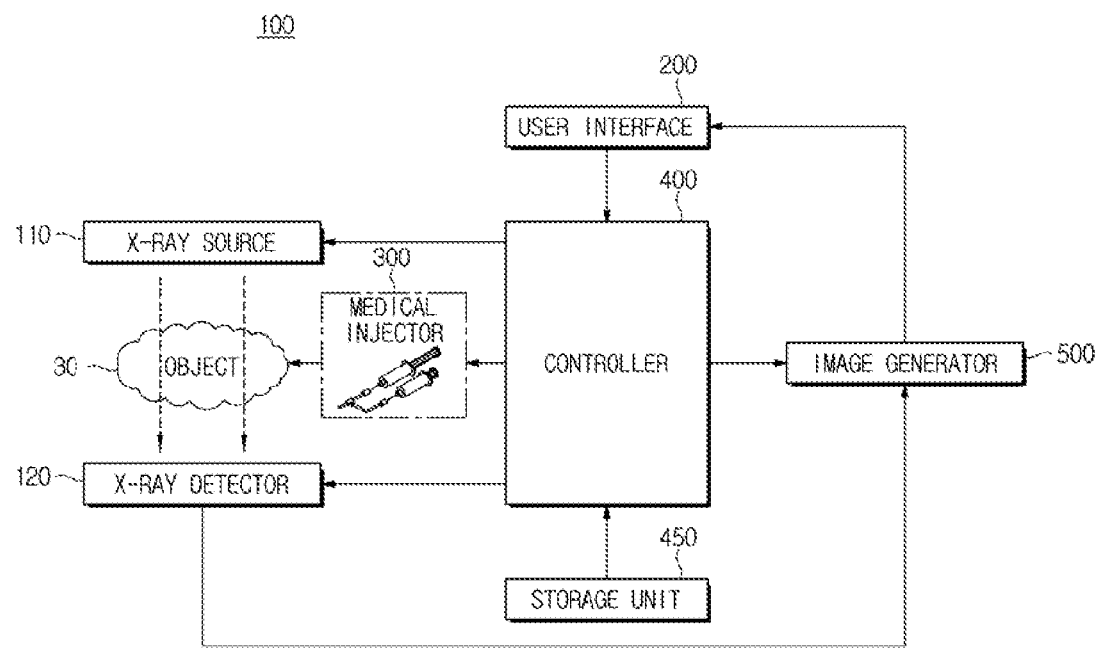
FIG. 5 is a control block diagram illustrating a medical imaging apparatus, according to an exemplary embodiment.

FIG. 5 is a control block diagram illustrating the medical imaging apparatus 100, according to an exemplary embodiment.

Referring to FIG. 5, the medical imaging apparatus 100 includes an X-ray source 110, an X-ray detector 120, a user interface 200, a medical injector 300, an image generator 500, a controller 400, and a storage unit (also referred to herein as a "storage device" and/or as a "storage") 450.

The X-ray source 110 is a device configured to generate X-rays and to emit the generated X-rays toward an object. The X-ray source 110 may include an X-ray tube (not shown) to generate X-rays, and the X-ray tube may include a bipolar vacuum tube including a cathode and an anode. The cathode may include a filament and a focusing electrode (or focusing cup) on which electrons are collected and may generate thermal electrons by heating the filament at a high temperature. However, the cathode is not limited to the filament, and may also include a carbon nano-tube operating at a high-speed pulse. The anode includes a target material disposed to face the cathode. When a high voltage is applied between the cathode and the anode, thermal electrons are accelerated and impinge on the target material of the anode, thereby generating X-rays.

The voltage applied between the cathode and the anode of the X-ray tube is referred to as a tube voltage and may be expressed as a peak value kvp. As the tube voltage increases, a speed of the thermal electrons increases, thereby increasing an energy of X-rays (photon energy) generated when the thermal electrons impinge on the target material. A current flowing in the X-ray tube is referred to as tube current and may be expressed as an average mA. As the tube current increases, an amount of X-rays (the number of photons of X-rays) increases. In particular, the energy of the X-rays may be adjusted by the tube voltage, and the amount of X-rays may be adjusted by the tube current and X-ray exposure time.

The X-ray source 100 emits X-rays via the X-ray tube before the contrast agent is injected into the object 30, and also emits X-rays in a state where the contrast agent is injected into the object 30.

First, the X-ray source 100 emits X-rays before the contrast agent is injected into the object 30. Before the contrast agent is injected into the object 30, the X-ray source 100 may emit X-rays at a fixed position in order to facilitate a setting of the ROI. X-rays may be emitted a plurality of number of times (i.e., at least two times) while the gantry 102 is not rotated and the X-ray source 100 is fixed at a predetermined position. While emitting X-rays, the table 190 on which the object 30 is lying may move in the D1 direction, and accordingly, the X-ray source 110 may emit X-rays toward various parts of the object 30. For example, the X-ray source 100 emits X-rays several times in a state of being fixed above the object 30 as illustrated in FIG. 3A, and the table 190 slowly moves in the D1 direction from a position in which the X-ray source 110 corresponds to the abdomen of the object 30 to perform X-rays irradiation on the lower part of the body of the object 30.

The X-ray source 110 may emit X-rays while rotating in order to facilitate a setting of a region to be monitored within the ROI before the contrast agent is injected into the object 30. When the X-ray source 110 emits X-rays at a fixed position and the ROI of the object 30 is set based thereon, the X-ray source 100 may emit X-rays at least twice while rotating around the ROI in accordance with the rotation of the gantry 100. However, for descriptive convenience, descriptions of emitting X-rays while the X-ray source 110 is rotated before injection of the contrast agent will not be given herein.

When the ROI is set and the test contrast agent is injected into the object 30, the X-ray source 100 emits X-rays toward the ROI. In this case, the gantry 102 does not rotate in the same manner as before injection of the contrast agent, and the X-ray source 100 may emit X-rays toward the ROI in a state of being fixed at a predetermined position at predetermined time intervals. The table 190 is fixed at a position where the X-ray source 100 corresponds to the ROI in order to allow emission of X-rays toward the ROI of the object 30 a plurality of number of times (i.e., at least twice).

The X-ray source 100 emits X-rays a plurality of number of times while rotating the area of diagnosis of the object 30 in accordance with rotation of the gantry 102 after the injection of the main contrast agent. In this case, the area of the diagnosis is a region to be diagnosed as selected by the user, and may be the same as or different from the ROI. When the ROI is different from the area of the diagnosis, the table 190 moves such that the X-ray source 110 correspond to the area of the diagnosis before X-ray irradiation. Accordingly, the X-ray source 110 emits X-rays toward the area of the diagnosis.

X-ray irradiation of the X-ray source 110 before and after the injection of the contrast agent will be described in more detail below with reference to controller 400 and the user interface 200.

The X-ray detector 120 is a device configured to detect X-rays that have been emitted from the X-ray source 110 and have propagated through the object 30. The X-ray detector 120 may also convert the detected X-rays into electric signals.

In general, X-ray detectors may be classified according to any one or more of material composition, conversion from detected X-rays into electric signals, and electric signal acquisition.

First, X-ray detectors may be classified into a single device mode and a hybrid device mode according to material composition. In the case of the single device mode, a part that detects X-rays and generates electric signals and a part that reads out and processes electric signals may be formed of a single semiconductor material or may be fabricated via a single process. In the case of the hybrid device mode, a part that detects X-rays and generates electric signals and a part that reads out and processes electric signals may be formed of different materials and/or may be fabricated via different processes.

X-ray detectors may be classified into a direct conversion mode and an indirect conversion mode, according to a mode of converting X-rays into electric signals. In the case of the direct conversion mode, electron-hole pairs are temporarily generated in a light receiving device if X-rays are emitted, and as a result of an electric field which is generated around both ends of the light receiving device, electrons move toward an anode and holes move toward a cathode. In this mode, an X-ray detector converts these movements into electric signals. In the case of the indirect conversion mode, photons having a visible light wavelength are discharged via reaction between X-rays emitted from the X-ray source and a scintillator, and a light receiving device senses the photons and converts the same into electric signals.

Further, X-ray detectors are classified, according to the electric signal acquisition move, into a charge integration mode in which a signal is acquired from charges after the charges are stored for a predetermined time, and a photon counting mode in which photons are counted whenever a signal is generated by a single X-ray photon.

The X-ray detector 120 may employ any of the modes described above and may detect X-rays that have passed through the object 30, convert the X-rays into electric signals, and transmit the converted electric signals to the controller 400 and/or to the image generator 500. The image generator 500 may generate an X-ray image based on the X-rays detected by the X-ray detector 120.

In particular, X-rays emitted from the X-ray source 100 pass through the object 30 and are detected by the X-ray detector 120, and the image generator 500 generates various X-ray images based on the detected X-rays. In this regard, a process including X-ray emission of the X-ray source 100 toward the object and X-ray detection of the X-ray detector 120 may be referred to as "scanning an object". Thus, a combination of the X-ray source 100 and the X-ray detector 120 may be referred to as a scanning unit and/or as a scanner.

As described above, the X-ray source 100 performs a first X-ray emission toward the object 30 before the contrast agent is injected thereinto, performs a second X-ray emission toward the object 30 in a state where the test contrast agent is injected into the object 30, and performs a third X-ray emission toward the object 30 in a state where the main contrast agent is injected into the object 30. Accordingly, the X-ray detector 120 performs first, second, and third X-ray detections in accordance therewith. The X-ray detector 120 performs the first X-ray detection in accordance with the first X-ray emission of the X-ray source 110, performs a second X-ray detection in accordance with the second X-ray emission of the X-ray source 110, and performs a third X-ray detection in accordance with the third X-ray emission of the X-ray source 110.

In particular, the medical imaging apparatus 100 primarily scans the object 30 before the contrast agent is injected into the object 30, secondarily scans the object 30 in a state where the test contrast agent is injected into the object 30, and thirdly scans the object 30 in a state where the main contrast agent is injected into the object 30 via the X-ray source 110 and the X-ray detector 120. In this regard, the primarily scanning the object 30 is referred to as "first scanning" and/or as "scout scanning", the secondarily scanning the object 30 is referred to as "second scanning" and/or as "ROI scanning", and the thirdly scanning the object 30 is referred to as "third scanning" and/or as "diagnostic scanning".

The medical injector 300 injects the contrast agent into the object 30 in order to facilitate a scanning of the object 30. The medical injector 300 sequentially inject the test contrast agent and the main contrast agent in accordance with a control signal of the controller 400 after the first scanning (or scout scanning) is terminated.

The contrast agent, as a marker which is capable of indicating a bloodstream, is a substance having a micro bubble structure that has a diameter of about 7 μm or less and stays in the bloodstream for about several minutes after being injected into the object 30. In particular, the contrast agent enhances the contrast in an image, importantly, during a radiographic diagnosis, by artificially increasing differences in X-ray absorption of tissues in order to improve visibility of tissues or blood vessels. In this aspect, the contrast agent is used to distinguish tissues or blood vessels in an image of the object by increasing differences in X-ray absorption.

Since the contrast agent increases differences in X-ray absorption, the injection of the contrast agent changes a brightness of the image. For example, as the contrast agent is injected into the object, X-ray absorption rates of tissues and blood vessels increase, thereby increasing the brightness of the image.

Since the contrast agent stays in the object for a limited time period, the brightness of the image varies as a function of time after the injection of the contrast agent. For example, the brightness continuously increases after the injection of the contrast agent and then returns to an original level after a predetermined time period. In particular, the brightness of the image has a peak. At the peak, the contrast of the image is maximized, and the greatest effect of the contrast agent is obtained. Thus, a time corresponding to the peak brightness of the image may be defined as a time when the contrast agent reaches an optimum state or, simply, as an optimum time of the contrast agent. The optimum time may be calculated, and the scanning of the object may be performed at the calculated optimum time.

The medical injector 300 calculates the optimum time of the contrast agent by injecting the test contrast agent before the injection of the main contrast agent, and scans the object while injecting the main contrast agent into the object based on the calculated optimum time. In particular, the medical injector 300 injects the test contrast agent, the X-ray source 110 and the X-ray detector 120 performs the second scanning (or ROI scanning) in correspondence with the injection of the test contrast agent, and the controller 400 calculates the optimum time of the contrast agent based on the acquired image. When the optimum time is calculated, the medical injector 300 injects the main contrast agent into the object, and the controller 400 controls the X-ray source 110 and the X-ray detector 120 to perform the third scanning (or diagnostic scanning) based on the optimum time.

Meanwhile, as the contrast agent is injected, the object may feel not only mild symptoms such as nausea, burning sensation, rash, sweating, itching, and pain at injection site, cough, vomiting, and dizziness, but also severe symptoms such as heart attack, myocardial infarction, and loss of consciousness. In order to test allergic reactions to the contrast agent as described above, the medical injector 300 injects the test contrast agent in a smaller amount than the main contrast agent which will be injected later. Amounts of the test contrast agent and the main contrast agent to be injected into the object by the medical injector 300 may be pre-set regardless of the object, and information relating thereto may be stored in the storage unit 450. Alternatively, amounts of the test contrast agent and the main contrast agent may vary according to the object, i.e., vary at every diagnosis, and information relating thereto may be input via the user interface 200.

The medical injector 300 may inject physiological saline immediately after the injection of the contrast agent. The medical injector 300 injects the physiological saline immediately after the injection of the test contrast agent such that the test contrast agent is pushed into the object 30 by a pressure caused by the physiological saline. The medical injector 300 may inject the physiological saline immediately after the injection of the main contrast agent such that the main contrast agent is pushed into the object 30 by a pressure caused by the physiological saline. In particular, the medical injector 300 may more efficiently inject the contrast agent into the object 30 as a result of the injection of the physiological saline.

The image generator 500 may generate an X-ray image in accordance with the scanning of the object and output the generated X-ray image to the user interface 200. The image generator 500 may generate a scout image in accordance with the first scanning (or scout scanning) of the object before the contrast agent is injected into the object, generate an ROI image in accordance with the second scanning (or ROI scanning) of the ROI in a state where the test contrast agent is injected, and generate a diagnostic image in accordance with the third scanning (or diagnostic scanning) of the area of diagnosis in a state where the main contrast agent is injected.

The image generator 500 may generate a graph illustrating variations in a brightness of an image of the ROI image or an image including the graph, and output the graph and/or the image to the user interface 200.

The generating and outputting of the image by the image generator 500 will be described in detail below with reference to FIGS. 6 to 10.

Figure 6:
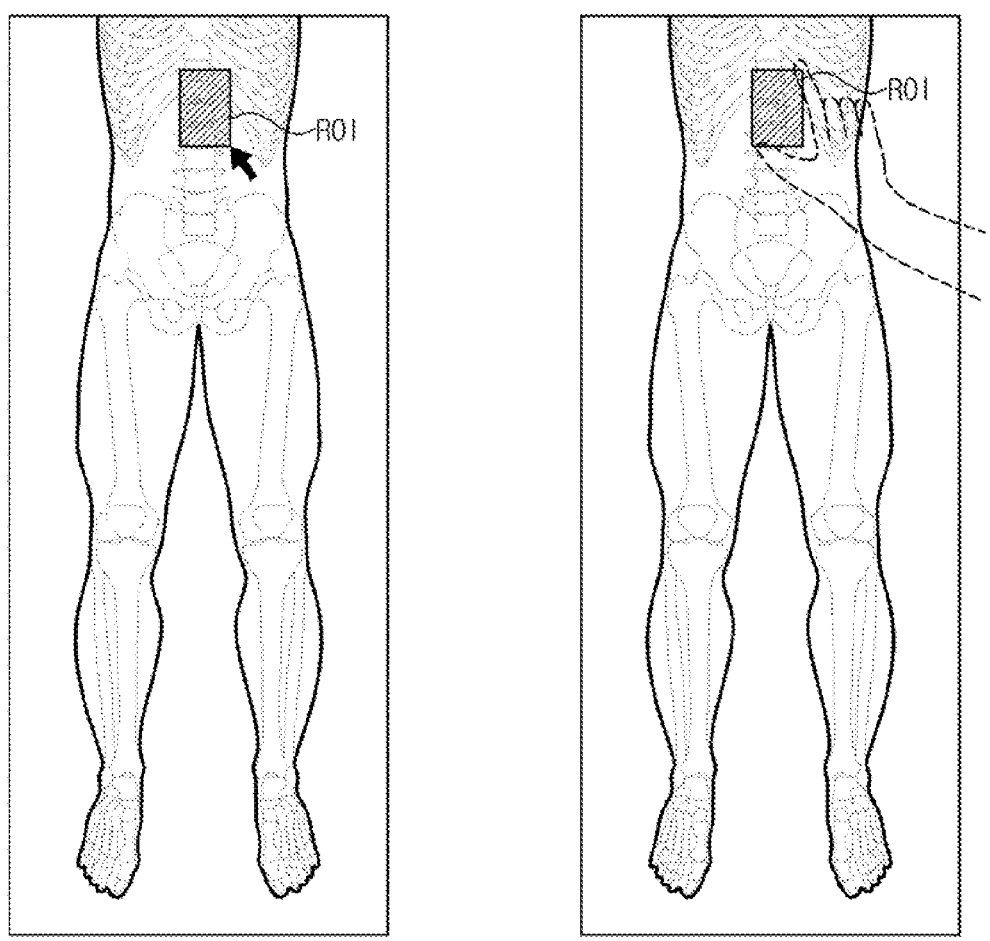
FIG. 6 is a diagram illustrating a generation of a scout image.

FIG. 6 is a diagram illustrating a generation of a scout image.

The user may select a region to be subjected to the first scanning (or scout scanning) via the user interface 200. For example, the user may select the entire body of the object as the region that is subject to a first scanning. Accordingly, the table 190 moves in the D1 direction such that the entire body of the object 30 passes between the X-ray source 110 and the X-ray detector 120, and the X-ray source 110 emits X-rays in a fixed state and the X-ray detector 120 detects X-rays in a fixed state in order to perform the first scanning on the entire body of the object 30.

Alternatively, the user may select the lower body of the object as the region to be subjected to the first scanning. In accordance with the user's selection, the table 190 moves in the D1 direction such that the lower body of the object 30 passes between the X-ray source 110 and the X-ray detector 120 from the abdomen, and the X-ray source 110 and the X-ray detector 120 respectively emit and detect X-rays in fixed states to perform the first scanning on the lower body of the object 30.

FIG. 6 illustrates a first scanning performed on the lower body. While the table 190 moves in the D1 direction, the X-ray source 110 and the X-ray detector 120 may emit and detect X-rays a plurality of number of times, respectively. In addition, the image generator 500 generates a plurality of X-ray images correspondingly with respect to positions to which X-rays are emitted and combines the X-ray images to correspond to the positions, thereby generating a single X-ray image as illustrated in FIG. 6. In this case, the single X-ray image is a scout image.

The generated scout image may be displayed on the user interface 200, and the user may select an ROI from within the displayed scout image. For example, the user may set the ROI by clicking one point of the scout image by using a mouse. Referring to the left diagram of FIG. 6, the ROI may be set in a predetermined size with respect to the clicked point. Alternatively, the user may directly touch the screen of the user interface 200 to set the ROI. Referring to the right diagram of FIG. 6, the user may drag a portion by using a hand, and the dragged portion may be set as the ROI.

When the ROI is set as described above and the user inputs a command to initiate an injection of the contrast agent via the user interface 200, the contrast agent filled in the medical injector 300 may be injected into the object 30. In this regard, the injected contrast agent is the test contrast agent, which is set to be injected in a smaller amount than the main contrast agent. Immediately after the injection of the test contrast agent, physiological saline may be injected into the object 30.

After the injection of the test contrast agent, a second scanning (or ROI scanning) is performed on the selected ROI. When the ROI is selected, the table 190 initiates moving in the D1 direction. When the ROI is located between the X-ray source 110 and the X-ray detector 120, the table 190 stops the moving and is fixed to prepare the second scanning. When the test contrast agent is injected into the object, the X-ray source 110 and the X-ray detector 120 repeat the emission and detection of X-rays in the fixed states at predetermined time intervals. In particular, during the second scanning, the region to be scanned is not changed, and a plurality of emissions and detections of X-rays are performed on the same ROI at predetermined time intervals.

The image generator 500 generates a plurality of X-ray images of the ROI correspondingly with respect to the X-ray emission times. In this regard, the generated X-ray images may include only the ROI or a peripheral region including the ROI. In this case, however, all of the X-ray images may include the same region formed of only the ROI or the peripheral region that includes the ROI. In addition, when the X-ray image includes the peripheral region that includes the ROI, the peripheral region has the same size.

A brightness or a contrast of a plurality of X-ray images of the ROI, i.e., the ROI images, varies according to the order of generation thereof as the contrast agent is injected.

The image generator 500 may obtain a graph that shows a variation in a brightness of the ROI images as a function of time and generate another image. The graphed image is an image monitoring variations in the brightness of the ROI images and may be defined as a monitoring image.

FIGS. 7A, 7B, 7C, and 7D are diagrams for describing a process of generating a monitoring image with time.

Figure 7A:
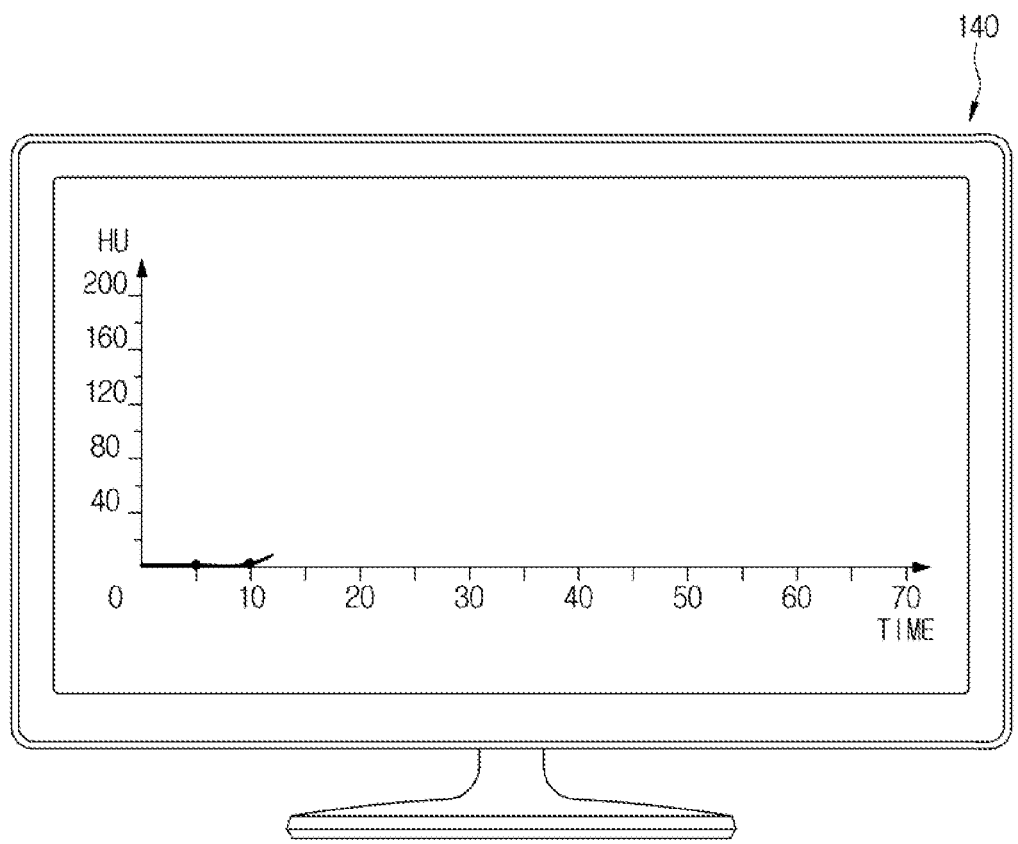
FIGS. 7A, 7B, 7C, and 7D are diagrams for describing a process of generating a monitoring image with time.

When the test contrast agent is injected into the object 30, the X-ray source 110 and the X-ray detector 120 scan the ROI at 5-second intervals, and the image generator 500 generates ROI images correspondingly thereto and generates a monitoring image in which a brightness of ROI images varies with time. As illustrated in FIG. 7A, the generated monitoring image may be output to the display apparatus 140 of the user interface 200. In this case, the brightness of the images may be measured by using a Hounsfield unit (HU) scale. FIG. 7A illustrates that a brightness of the ROI or the ROI image is 0 HU at 5 seconds and at 10 seconds after the injection of the contrast agent, which is the same as that before the injection of the contrast agent. This indicates that a predetermined time period is required for the test contrast agent to arrive at the ROI.

The image generator 500 calculates a brightness at times other than times at which the brightness is obtained via the ROI image by using an average of the brightnesses at two known times. Also, the image generator 500 calculates the brightness between times at which the brightness is obtained via the ROI image in the same manner. Thus, the brightness of the ROI image may be output as a linear or curved graph.

Figure 7B:
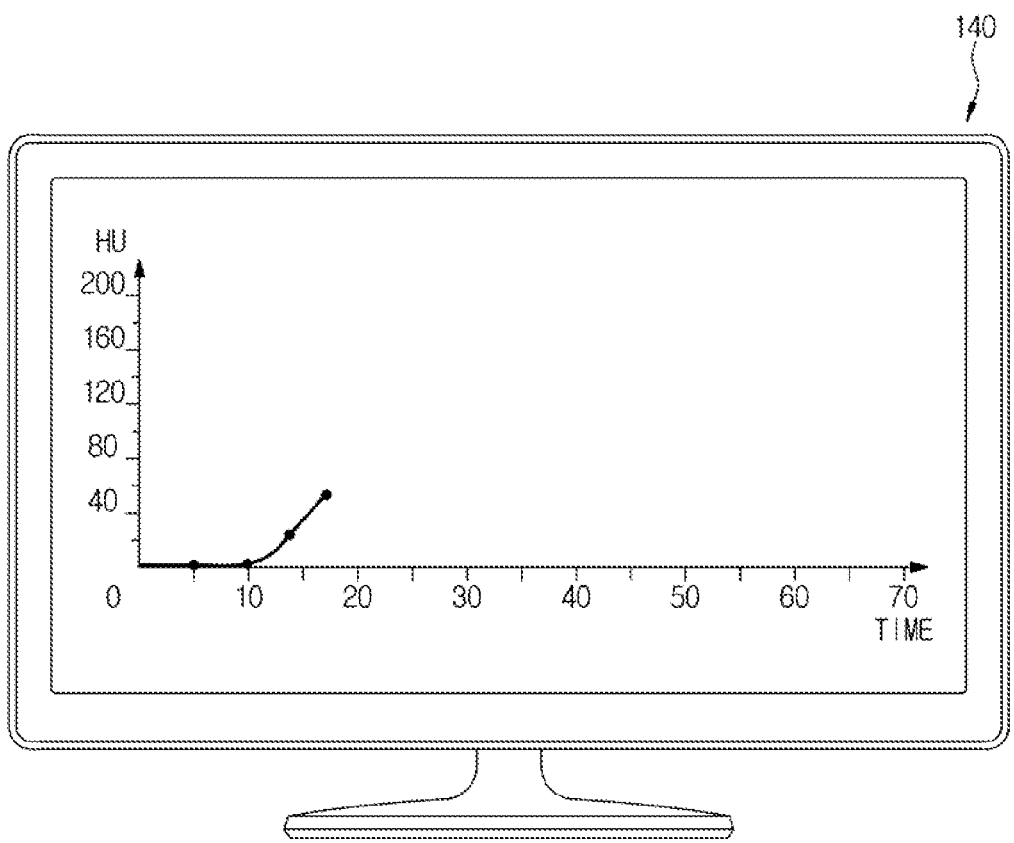

When the contrast agent arrives at the ROI, the brightness of the ROI image increases, and correspondingly, the image generator 500 outputs the monitoring image in which the brightness gradually increases. As illustrated in FIG. 7B, the image generator 500 may generate a monitoring image indicating that the brightness increases to 30 HU and 60 HU after 10 seconds.

Meanwhile, as the brightness of the ROI image increases, the X-ray source 110 and the X-ray detector 120 may scan the object at shorter time intervals. For example, as illustrated in FIG. 7A, the ROI may be scanned at 5 second intervals. As the brightness increases, the scanning time interval may be reduced such that the ROI may be scanned at 4 second intervals or 3 second intervals, as illustrated in FIG. 7B.

Figure 7C:
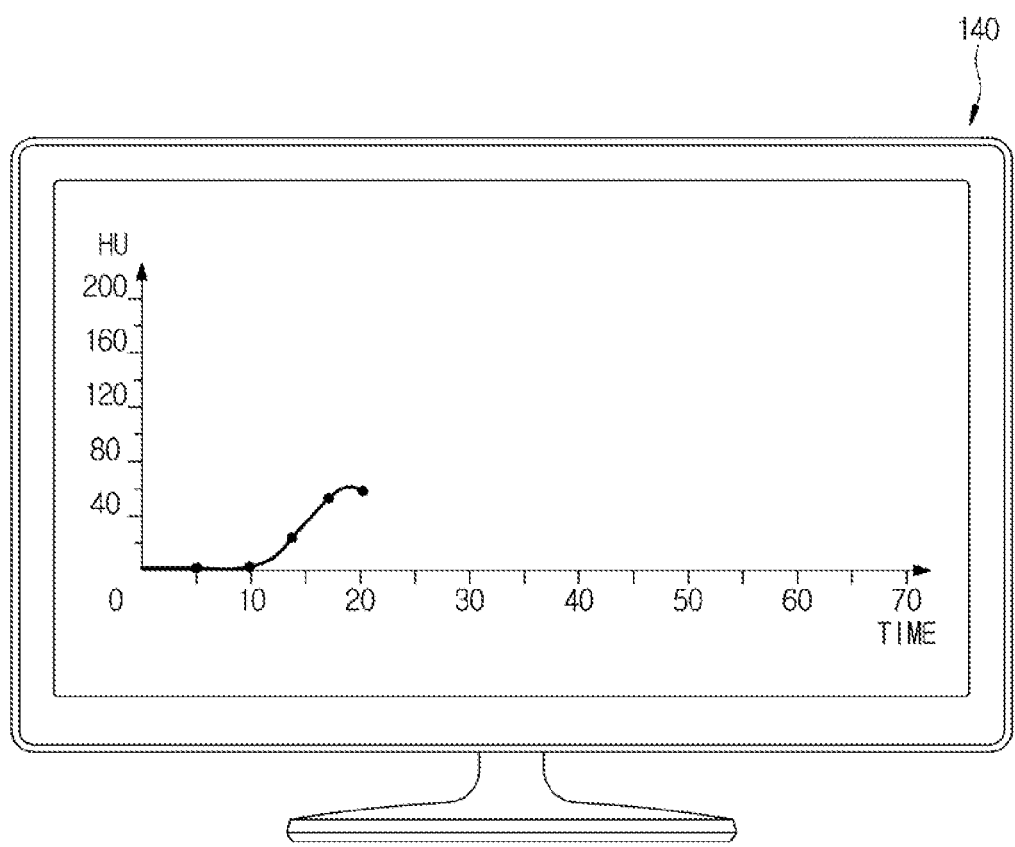
Figure 7D:
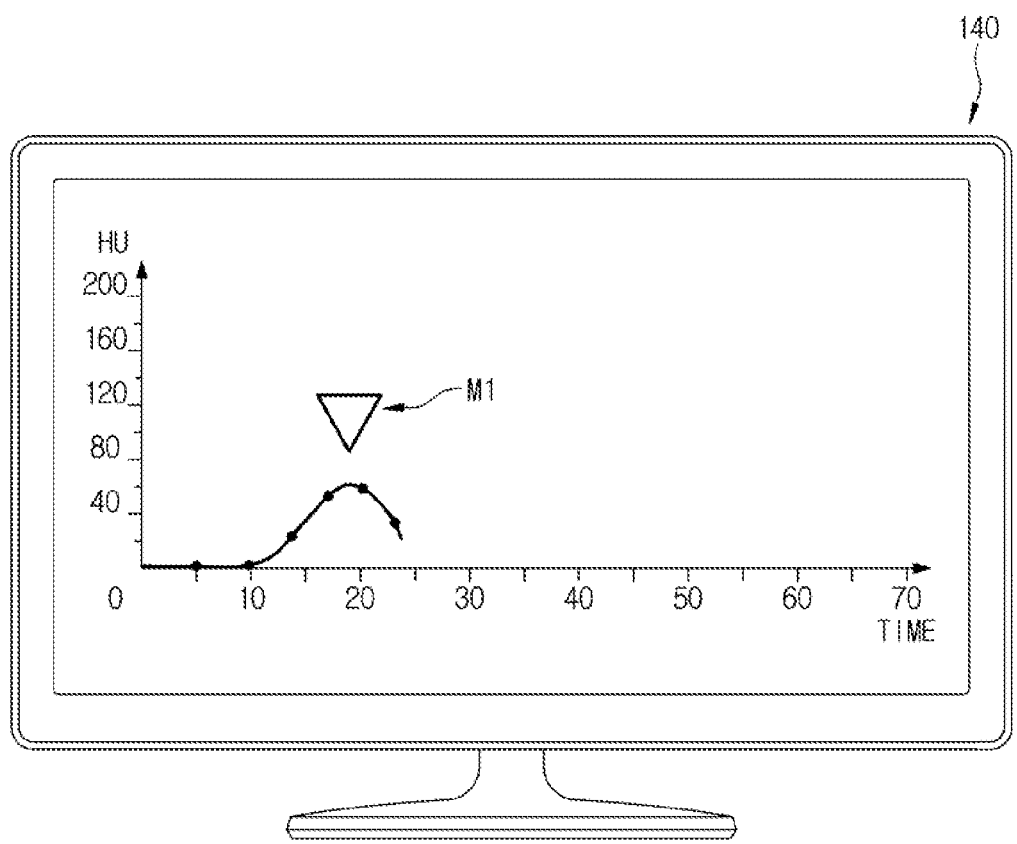

As the ROI is scanned at the adjusted time intervals, the image generator 500 may generate a monitoring image including a peak brightness, as illustrated in FIG. 7C. Also, the image generator 500 may detect the peak, create a mark M1 to indicate the peak, and output the peak together with the mark M1, as illustrated in FIG. 7D. In this regard, information relating to a time when the peak occurs (i.e., a peak-occurrence time) or a time period from injection of the test contrast agent to the peak may be stored in the storage unit 450.

Figure 8A:
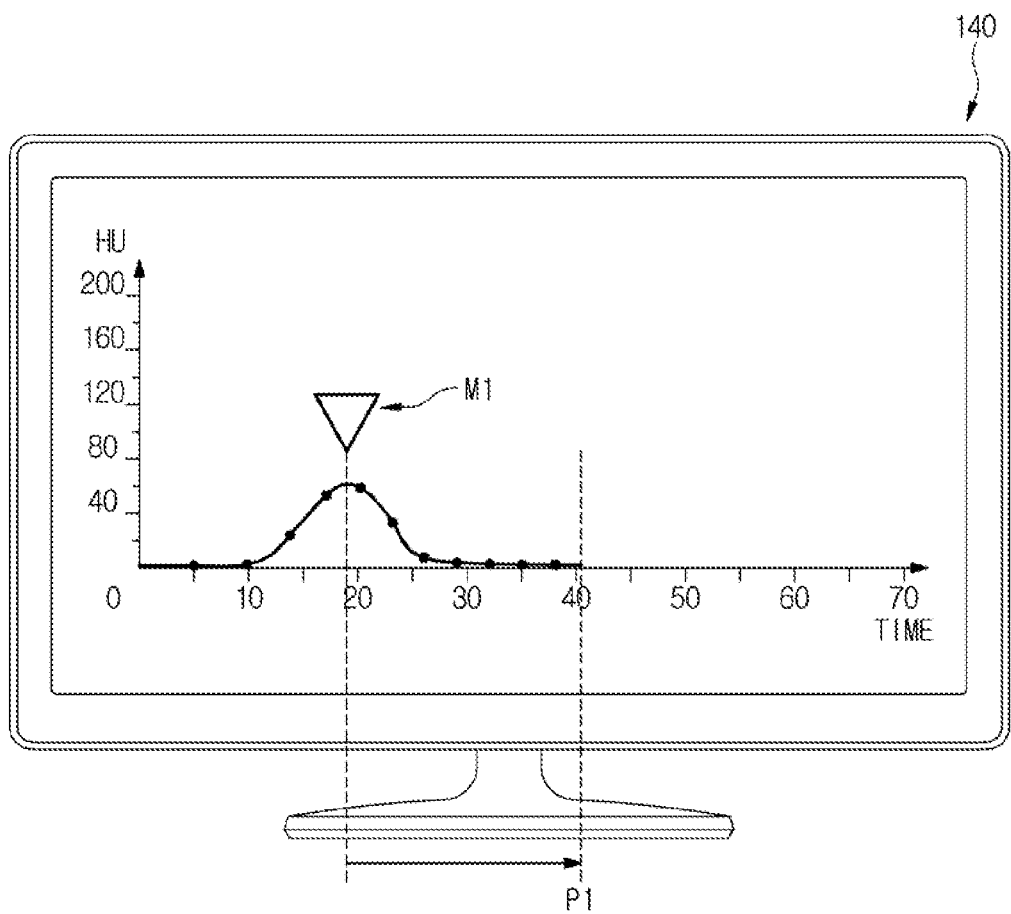
FIGS. 8A and 8B are diagrams for describing a process of terminating a monitoring image.
Figure 8B:
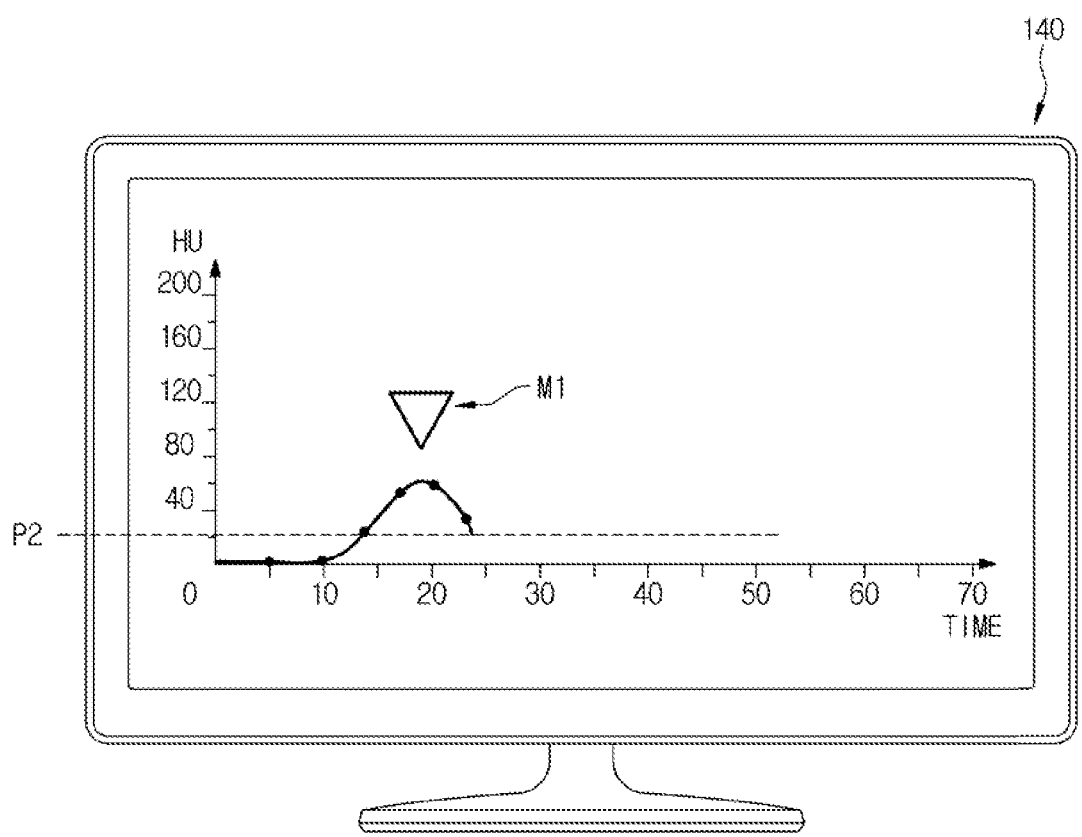

FIGS. 8A and 8B are diagrams for describing a process of terminating the monitoring image.

When the peak is detected and the mark is created above the peak in the monitoring image, the image generator 500 terminates the generating of the monitoring image. For example, the image generator 500 may continue the generating of the monitoring image for a time period P1 from the detected peak and then terminate the generating of the monitoring image after the time period P1, as illustrated in FIG. 8A. Alternatively, as illustrated in FIG. 8B, the image generator 500 may terminate the generating of the monitoring image at a time when the brightness of the ROI or the ROI image becomes lower than a brightness P2, which is set to be lower than the peak value, after the peak. In this regard, P1 or P2 may be pre-set and stored in the storage unit 450.

The image generator 500 may create the mark M1 having an inverted triangle shape such that a lower vertex of the inverted triangle indicates the peak-occurrence time, as illustrated in FIG. 7D. However, the mark indicating the peak may have any of various other shapes in addition to the shape illustrated in FIG. 7D.

Figure 9A:
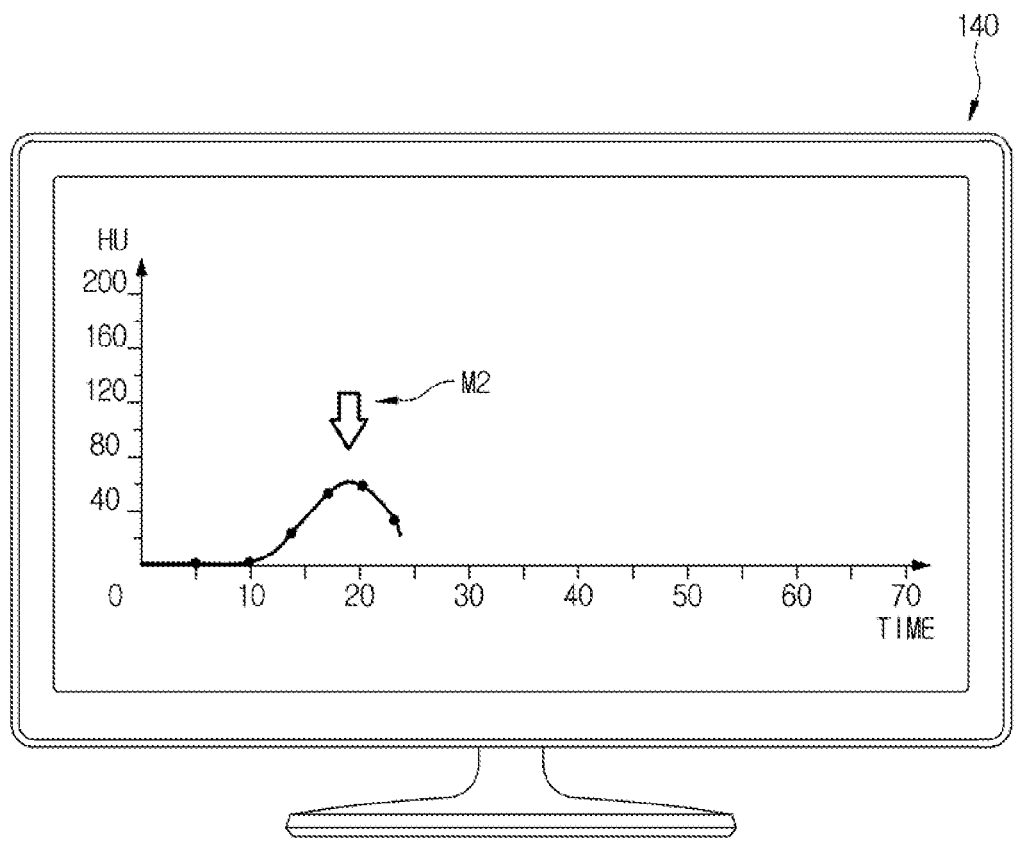
FIGS. 9A and 9B are diagrams illustrating examples of generating a mark that indicates a peak.
Figure 9B:
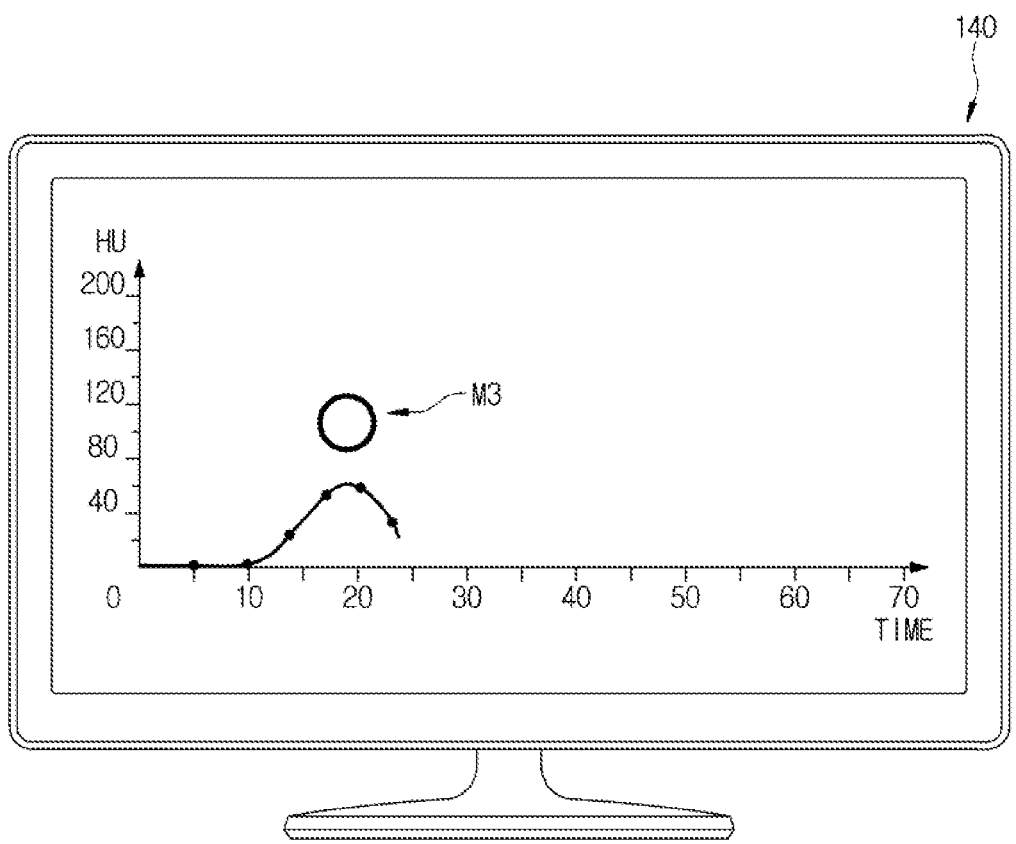

FIGS. 9A and 9B are diagrams illustrating examples of generating a mark that indicates a peak.

As illustrated in FIG. 9A, the image generator 500 may create a mark M2 having an arrow shape and indicating the peak-occurrence time. As illustrated in FIG. 9B, the image generator 500 may also create a mark M3 having a circular shape, the center of which indicates the peak-occurrence time. However, these are examples of the mark, and the shape of the mark is not limited thereto.

The user may identify the monitoring image output via the display apparatus 140 and the mark created thereon and confirm whether the mark correctly indicates the peak.

Figure 10A:
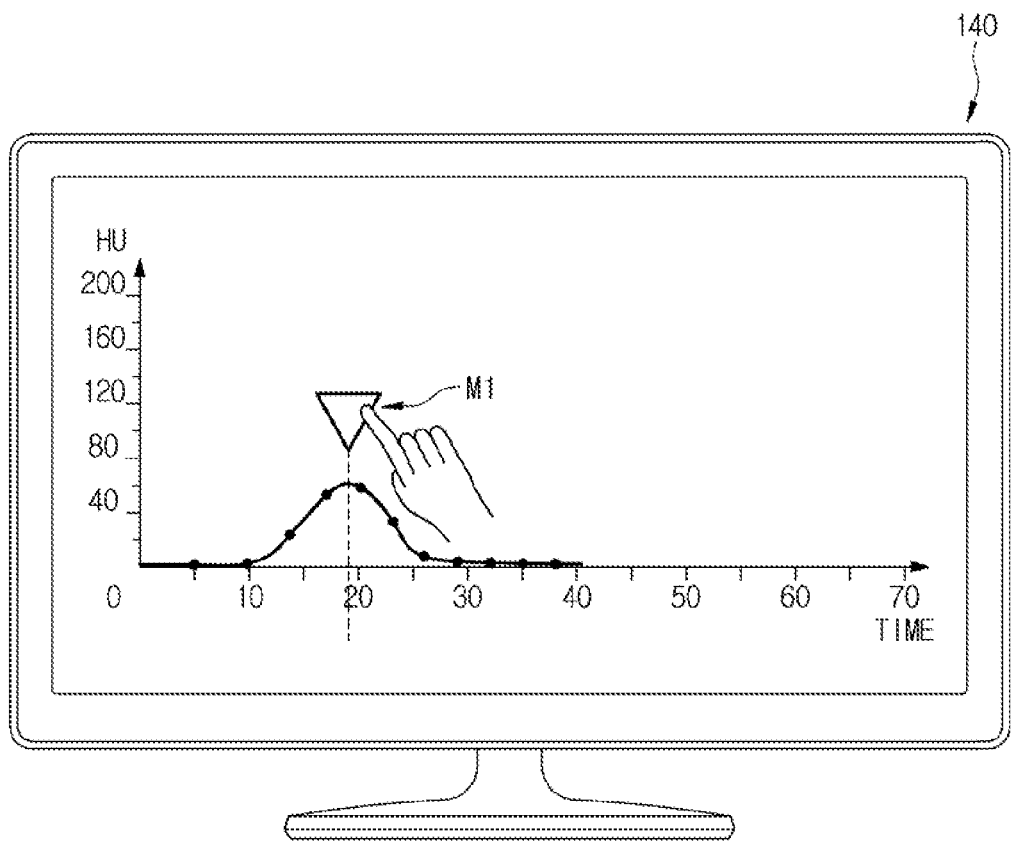
FIGS. 10A and 10B are diagrams for describing a user's confirmation of a mark.
Figure 10B:
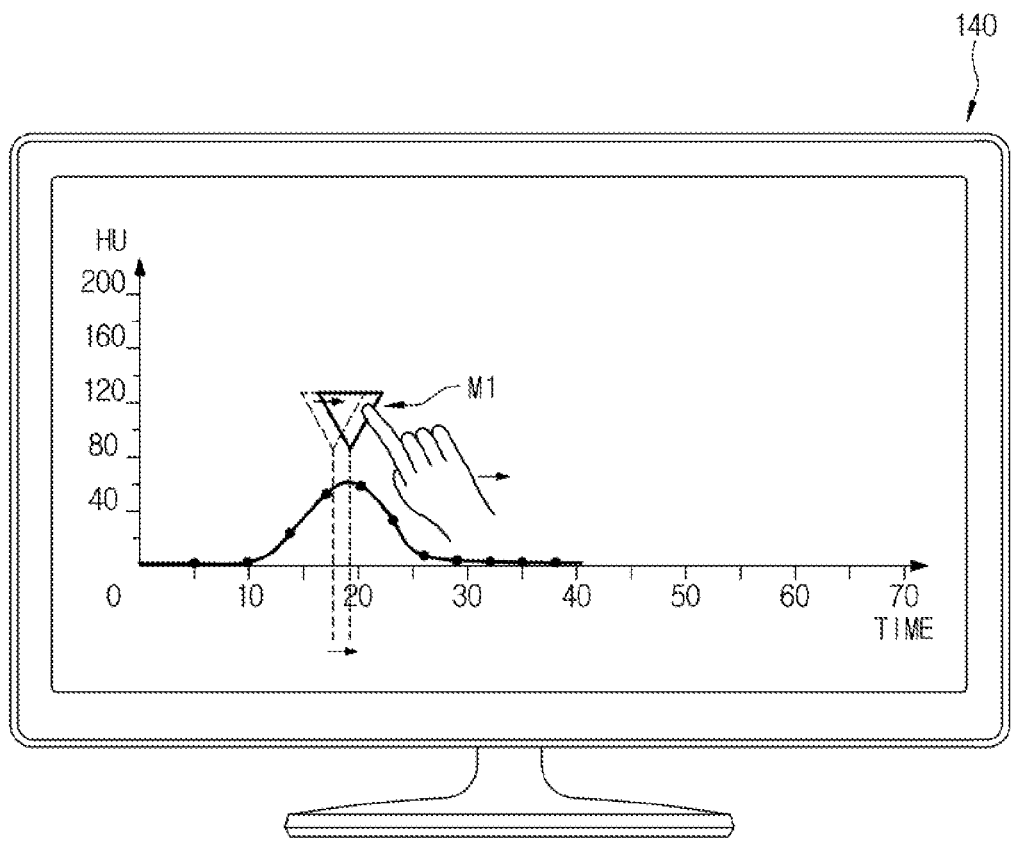

FIGS. 10A and 10B are diagrams for describing a user's confirmation of a mark.

As described above, the image generator 500 generates a monitoring image in which a brightness varies with time, creates a mark indicating the peak brightness, and outputs the monitoring image and the mark to the display apparatus 140. The user may examine the monitoring image and the mark displayed on the display apparatus 140 and confirm that the mark is created at a position that indicates the peak-occurrence time. As illustrated in FIG. 10A, as a recognition that the position of the mark M1 corresponds to the peak occurrence time, the user may touch the mark M1 displayed on the screen to finally confirm the mark M1. The user may also click the mark M1 by using a mouse or may press an enter key of a keyboard in an alternative exemplary embodiment with respect to FIG. 10A, instead of directly touching the mark M1 on the screen for the final confirmation.

When the position of the mark M1 does not correspond to the peak-occurrence time as illustrated in FIG. 10B, the user may drag the mark M1 displayed on the screen to change the position of the mark M1. The user may also use a hardware device, such as a mouse, instead of directly dragging the mark M1 displayed on the screen in order to change the position of the mark M1. The image generator 500 may change the position of the mark M1 in accordance of the user's drag motion to create and output a new monitoring image. As the position of the mark M1 is changed, the peak-occurrence time or the time period from injection of the test contrast agent to the peak, which are previously stored in the storage unit 450, may be corrected and stored in the storage unit 450.

Meanwhile, if a user's confirmation command, such as clicking or dragging, is not received within a predetermined time period, the image generator 500 may recognize that the current position of the mark correctly indicates the position of the peak as a default. The predetermined time period for the user's confirmation may be pre-set and stored in the storage unit 450.

The image generator 500 may generate a diagnostic image in accordance with the third scanning (or diagnostic scanning) of the area of the diagnosis in a state where the main contrast agent is injected into the object. In this regard, the area of the diagnosis may be the same as or different from the selected ROI as described above. The controller 400 calculates a starting time of the third scanning based on the time period from the injection of the test contrast agent to the peak, and controls a rotation of the gantry 102 and X-ray emission of the X-ray source 110 in order to perform the third scanning operation according to the calculated time.

The image generator 500 generates a plurality of X-ray images of the area of diagnosis in accordance with the third scanning. In this regard, the generated X-ray images, i.e., the diagnostic images, may include 2D cross-sectional images acquired while the gantry 102 rotates. If the scout image or the ROI image is a 2D projected image of the x-y plane (a plane formed by the x-axis and the y-axis), the diagnostic image may be a 2D projected image of the x-z plane (i.e., a plane formed by the x-axis and the z-axis). The image generator 500 may generate a 3D diagnostic image by combining the 2D projected images of the x-z plane. The 3D diagnostic image may include a 3D image and/or a 3D stereo image.

The controller 400 controls an overall operation of the medical imaging apparatus 100.

For example, the controller 400 may control the gantry 102 to be fixed or rotated, i.e., the X-ray source 100 and the X-ray detector 120 to be fixed or rotated, and may control the table 190 to be fixed or rotated.

Alternatively, the controller 400 may control a time of emitting X-rays by the X-ray source 110 and/or an amount of X-rays to be emitted from the X-ray source 110.

The controller 400 may generate a control signal to perform a first scanning (or scout scanning) in accordance with the user's input via the user interface 200. In particular, the user may input a region to be subjected to the first scanning before the injection of the contrast agent and input a command to initiate the first scanning. Accordingly, the controller 400 controls the table 190 to move and controls the X-ray source 110 to emit X-rays.

The controller 400 may generate a control signal to perform a second scanning (or ROI scanning) in accordance with the injection of the test contrast agent. The controller 400 controls the table 190 to move correspondingly to the selected ROI. When the user inputs a command to initiate the injection of the test contrast agent, the controller 400 controls the X-ray source 110 to emit X-rays toward the ROI at predetermined time intervals. The controller 400 may control a time of terminating the second scanning.

The controller 400 may generate a control signal to perform a third scanning (i.e., diagnostic scanning) in accordance with the injection of the main contrast agent. The controller 400 may calculate a peak to be acquired when the main contrast agent is injected into the object by using the peak acquired by the injection of the test contrast agent to perform the third scanning and may calculate a starting time of the third scanning based thereon. In addition, the controller 400 may control the X-ray source 110 to emit X-rays at the calculated time. This will be described in more detail with reference to FIG. 11. In this regard, the peak acquired by the injection of the test contrast agent is simply referred to as "peak of test contrast agent", and the peak to be acquired by injection of the main contrast agent is simply referred to as "peak of main contrast agent".

Figure 11:
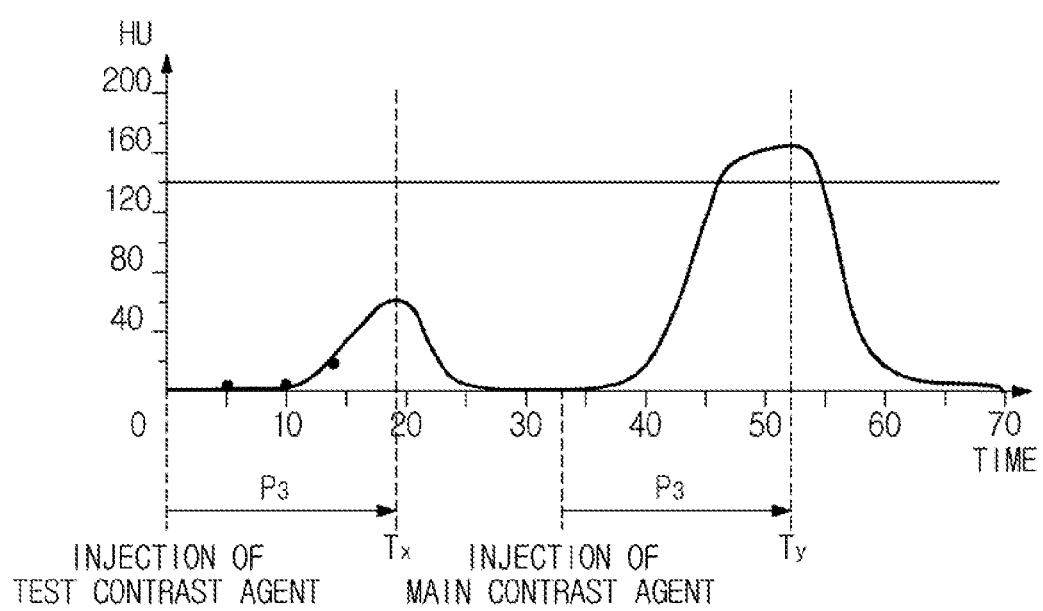
FIG. 11 is a diagram for describing a method of calculating a peak of a main contrast agent to perform a diagnostic imaging procedure.

FIG. 11 is a diagram for describing a method for calculating a peak of a main contrast agent to perform a diagnostic imaging procedure.

As described above with reference to FIGS. 10A and 10B, when the user confirms the position of the mark by clicking, or the like, or changes the position of the mark by dragging, or the like, the peak of the test contrast agent, and more particularly, a peak-occurrence time is finally determined. In FIG. 11, the peak-occurrence time of the test contrast agent is finally determined as Tx. The controller 400 acquires a time period P3 from the injection of the test contrast agent to the peak by using the finally determined time Tx. The controller 400 calculates the peak, more specifically, the peak-occurrence time, of the main contrast agent based on the time period P3. The controller 400 calculates a time after the time period P3 from the injection of the main contrast agent as a peak-occurrence time Ty of the main contrast agent.

The controller 400 calculates a starting time of the third scanning (or diagnostic scanning) based on a distance from the ROI to the area of the diagnosis or the arrival time period of the contrast agent at the area of the diagnosis from the ROI. In this regard, the distance from the ROI to the area of the diagnosis or the arrival time period of the contrast agent at the area of the diagnosis from the ROI may be pre-stored in the storage unit 450.

When the distance from the ROI to the area of the diagnosis is stored in the storage unit 450, the controller 400 acquires an arrival time period P4 of the contrast agent at the area of the diagnosis from the ROI based on a distance S1 from an injection site of the contrast agent to the ROI, a distance S2 from the ROI to the area of the diagnosis, and a time period P3 taken (or to be taken) from injection of the test (or main) contrast agent to the peak, and calculates the starting time of the third scanning based on the acquired arrival time period P4 of the contrast agent.

For example, the controller 400 may acquire the arrival time period P4 via an application of a proportional expression S1:S2=P3:P4, and may calculate the starting time of the third scanning as a time after P3+P4 from the injection of the main contrast agent.

When an arrival time period P5 of the contrast agent at the area of diagnosis from the ROI is stored in the storage unit 450, the controller 400 may calculate the stating time of the third scanning by using the time period P3 taken (or to be taken) from the injection of the test (or main) contrast agent to the peak and the arrival time period P5 of the contrast agent stored in the storage unit 450. In this aspect, the controller 400 may calculate the starting time of the third scanning as a time after P3+P5 from the injection of the main contrast agent.

An arrival time period P6 of the contrast agent at the ROI from the injection site of the contrast agent and the arrival time period P5 of the contrast agent at the area of the diagnosis from the ROI may be stored in the storage unit 450. In this case, the controller 450 may correct the arrival time period P5 of the contrast agent stored in the storage unit 450 based on a difference between an actual time period P3 taken (or to be taken) from injection of the test (or main) contrast agent to the peak and the arrival time period P6 of the contrast agent stored in the storage unit 450, and may calculate the starting time of the third scanning by using the time period P3 and the corrected arrival time period P5. In particular, if the corrected arrival time period P5 is referred to as P7, the controller 400 may calculate the starting time of the third scanning as a time after P3+P7 from the injection of the main contrast agent.

The controller 400 may control the X-ray source 110 to emit X-rays at the calculated starting time of the third scanning. The controller 400 controls the table 190 to move correspondingly with respect to the area of the diagnosis, the gantry 102 to rotate at a predetermined speed at the calculated starting time of the third scanning, and the X-ray source 110 mounted on the gantry 102 to emit X-rays at predetermined time intervals.

The controller 400 may control the image generator 500 to generate a scout image, an ROI image, and a diagnostic image in response to the first scanning (or scout scanning), the second scanning (or ROI scanning), and the third scanning (or diagnostic scanning). The controller 400 may control the image generator 500 to generate a monitoring image from the ROI image. In addition, the controller 400 may control the user interface 200 to display at least one image selected from the group consisting of the scout image, the ROI image, the diagnostic image, and the monitoring image.

The controller 400 may control the time of the injection of the contrast agent into the object 30. In particular, when the user inputs a command to inject the test contrast agent via the user interface 200, the controller 400 generates a control signal to initiate an injection of the test contrast agent in accordance therewith and outputs the control signal to the medical injector 300. Also, when the user inputs a command to inject the main contrast agent, the controller 400 may generate a control signal to initiate an injection of the main contrast agent in accordance therewith and outputs the control signal to the medical injector 300. Alternatively, the controller 400 may generate a control signal such that the main contrast agent is injected at a predetermined time.

For example, the main contrast agent may be pre-set to be injected at the peak-occurrence time of the test contrast agent, and the controller 400 may generate a control signal to initiate the injection of the main contrast agent in accordance therewith. Alternatively, the main contrast agent may be pre-set to be injected at a time after a predetermined time period, e.g., after 5 seconds, from the peak-occurrence time of the test contrast agent, and the controller vane 400 may generate a control signal to initiate the injection of the main contrast agent in accordance therewith.

The user interface 200 may receive an instruction or command to control an operation of the medical imaging apparatus 100 from the user and provide various screens related to operation of the medical imaging apparatus 100.

The user interface 200 may input a scanning command to perform any of the first scanning (or scout scanning), the second scanning (or ROI scanning), and/or the third scanning (or diagnostic scanning).

The user interface 200 may facilitate an input of a command to inject the contrast agent. The user interface 200 may facilitate an input of at least one of a command to inject the test contrast agent and a command to inject the main contrast agent.

The user interface 200 may display at least one image from among the scout image, the ROI image, and the diagnostic image generated in accordance with the first scanning (or scout scanning), the second scanning (or ROI scanning), and the third scanning (or diagnostic scanning).

The user interface 200 may display the monitoring image generated based on the ROI image. In particular, the user interface 200 may display the monitoring image including a peak-occurrence process of the test contrast agent. The user interface 200 may display a monitoring image in which the peak of the test contrast agent is indicated by a mark.

The user interface 200 may receive a confirmation of the peak of the test contrast agent from the user. The user may confirm the position of the mark by clicking or change the position of the mark by dragging via the user interface 200 to finally determine the time of the test contrast agent.

The storage unit 450 may store data and/or an algorithm which relate to a manipulation of the medical imaging apparatus 100.

The storage unit 450 may store information relating to injection amounts of the test contrast agent and the main contrast agent. The storage unit 450 may store a limited time period for receiving the confirmation of the position of the mark. The storage unit 450 may store may store a peak-occurrence time of the test contrast agent or a time period from injection of the test contrast agent to the peak. The storage unit 450 may store a reference time period P1 and/or a reference brightness P2 to terminate generation of the monitoring image. The storage unit 450 may store a distance from the ROI to the area of the diagnosis or an arrival time period of the contrast agent at the area of the diagnosis from the ROI.

The storage unit 450 may store an algorithm that facilitates a setting of the ROI in accordance with the user's input. The storage unit 450 may store an algorithm to generate at least one image of the scout image, the ROI image, and the diagnostic image in accordance with the first scanning (or scout scanning), the second scanning (or ROI scanning), and the third scanning (or diagnostic scanning). The storage unit 450 may store an algorithm to generate the monitoring image based on the ROI image. The storage unit 450 may store an algorithm to generate the peak of the main contrast agent based on the peak of the test contrast agent. The storage unit 450 may store an algorithm to calculate the starting time of the third scanning based on the peak of the test contrast agent or based on the calculated peak of the main contrast agent.

The storage unit 450 may be implemented as non-volatile memory devices such as any one or more of Read Only Memory (ROM), Programmable Read Only Memory (PROM), Erasable Programmable Read Only Memory (EPROM), and flash memory, volatile memory devices such as Random Access Memory (RAM), or storage devices such as hard disk drive sand optical disc drives. However, the storage unit 450 is not limited thereto, and any other known storage units may also be used.

Figure 12:
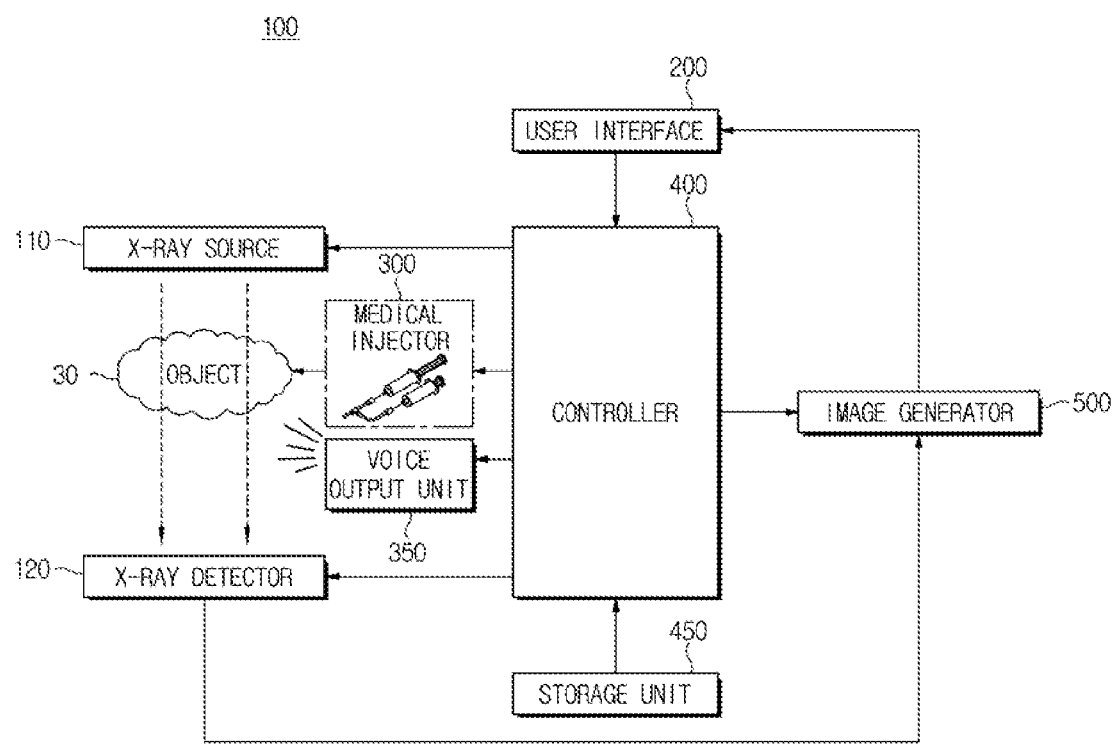
FIG. 12 is a control block diagram illustrating a medical imaging apparatus, according to another exemplary embodiment.

FIG. 12 is a control block diagram illustrating a medical imaging apparatus 100, according to another exemplary embodiment.

Referring to FIG. 12, the medical imaging apparatus 100 may include an X-ray source 110, an X-ray detector 120, a user interface 200, a medical injector 300, a voice output unit (also referred to herein as a "voice output device") 350, an image generator 500, a controller 400, and a storage unit 450. In particular, the medical imaging apparatus 100 of FIG. 12 may further include the voice output unit 350 as compared with that of FIG. 5. Hereinafter, the same descriptions given above with reference to FIG. 5 will not be repeated.

The voice output unit 350 is configured to output a guidance message "Hold your breath" to the object 30 based on the calculated peak of the main contrast agent or the starting time of the third scanning.

Figure 13A:
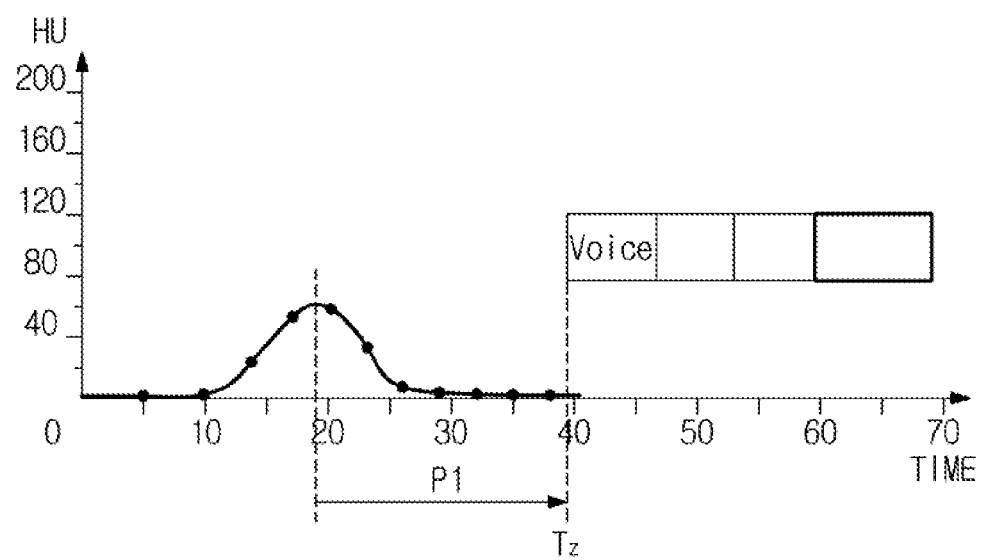
FIGS. 13A, 13B, and 13C are diagrams illustrating a process of outputting a message by a voice output unit.
Figure 13B:
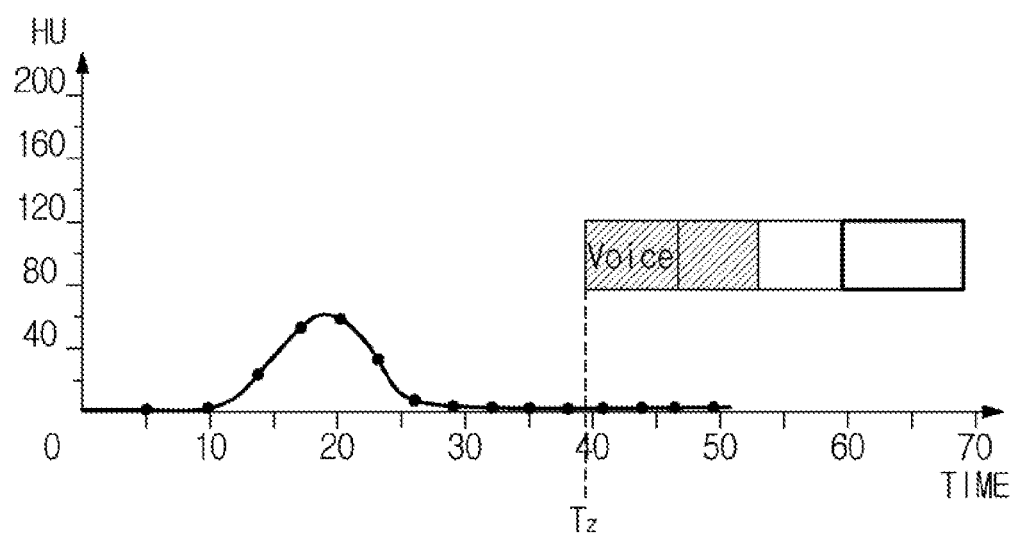
Figure 13C:
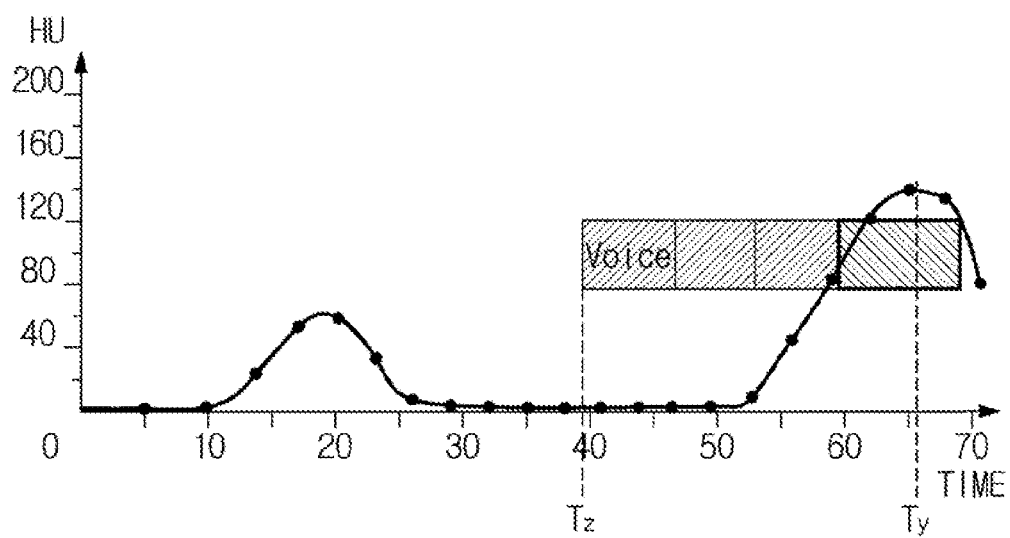

FIGS. 13A, 13B, and 13C are diagrams illustrating a process of outputting a message by a voice output unit.

As described above with reference to FIG. 10A, the generating of the monitoring image may be terminated after the time period P1 from the peak-occurrence time. In this regard, a time of terminating the generating of the monitoring image may be referred to as Tz.

As illustrated in FIG. 13A, the voice output unit 350 may perform a preparation process for outputting the guidance message from the time Tz. When the controller 400 calculates the peak of the main contrast agent or the starting time of the third scanning, the voice output unit 350 continues a preparation for outputting the guidance message while the main contrast agent arrives at the ROI as illustrated in FIG. 13B or before the calculated peak of the main contrast agent. At the peak of the main contrast agent, as illustrated in FIG. 13C, the voice output unit 350 informs the object of an initiation of the third scanning by outputting the guidance message "Hold your breath" to the object 30. By outputting the guidance message, an artifact of the diagnostic image caused by breathing during the third scanning may be reduced.

In particular, since the controller 400 accurately calculates the peak of the main contrast agent, an artifact of a final diagnostic image may be reduced.

Meanwhile, FIGS. 13A, 13B, and 13C illustrate examples of the process of outputting the message, and the voice outputting time may vary. For example, the voice output unit 350 may output the guidance message between the calculated peak of the main contrast agent and the starting time of the third scanning calculated based thereon.

The controller 400 may control the outputting of the guidance message by the voice output unit 350 based on the calculated peak of the main contrast agent or the starting time of the third scanning. The storage unit 450 may store an algorithm to output the guidance message.

The medical imaging apparatus in which the time of injecting the contrast agent and the time of the X-ray scanning are controlled is described above with reference to the illustrated control block diagram. Hereinafter, a method of controlling the medical imaging apparatus will be described with reference to a flowchart.

Figure 14:
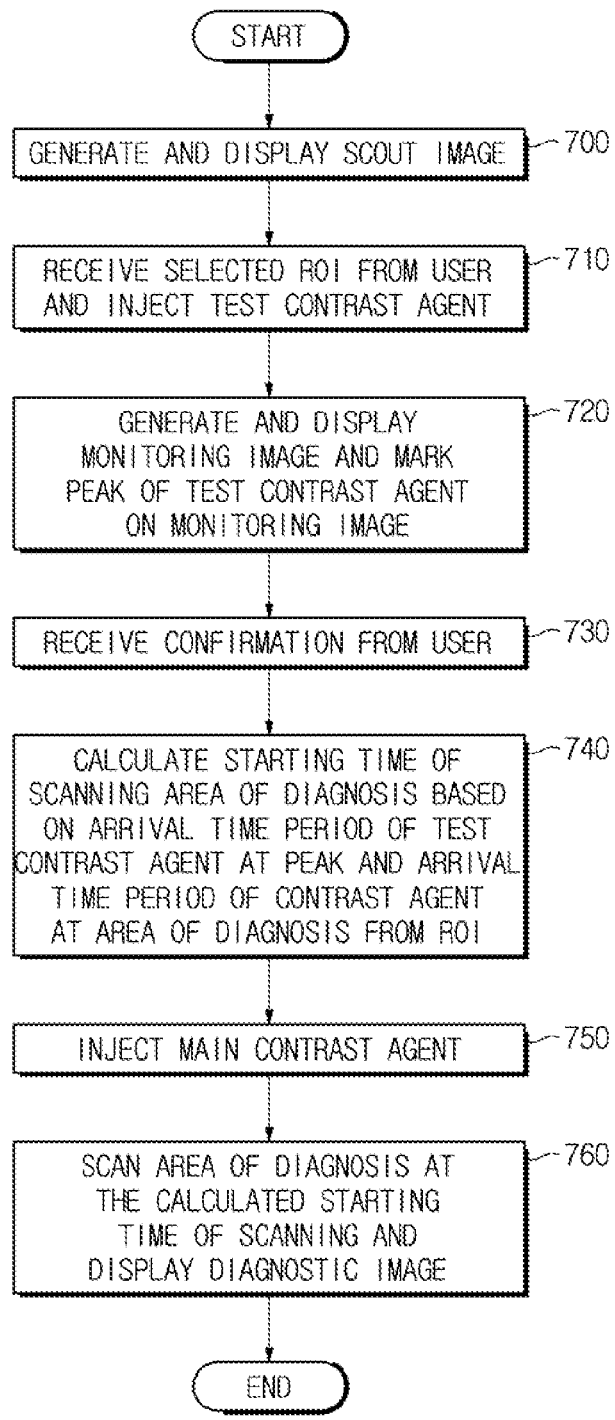
FIG. 14 is a flowchart illustrating a method for controlling a medical imaging apparatus, according to an exemplary embodiment.

FIG. 14 is a flowchart illustrating a method for controlling a medical imaging apparatus, according to an exemplary embodiment.

Referring to FIG. 14, in operation 700, the medical imaging apparatus 100 generates a scout image and displays the scout image on the user interface 200.

First, the user may select a region to be subjected to the first scanning (or scout scanning) via the user interface 200. The medical imaging apparatus 100 allows the selected region to pass between the X-ray source 110 and the X-ray detector 120 by moving the table 190. Also, the medical imaging apparatus 100 controls the X-ray source 110 to emit X-rays and the X-ray detector 120 to detect X-rays at fixed positions while the table 190 moves in order to perform the first scanning on the selected region.

The medical imaging apparatus 100 generates a scout image in accordance with the first scanning and displays the generated scout image such that the user confirms the scout image.

In operation 710, when the user selects an ROI on the scout image, the medical imaging apparatus 100 injects the test contrast agent into the object.

The user may select the ROI by using a hardware device such as a mouse, or by touching or dragging the screen of the user interface 200 with a hand or a finger.

When the ROI is selected, the medical imaging apparatus 100 injects the test contrast agent into the object via the medical injector 300. The user inputs a command to inject the test contrast agent via the user interface 200, and the medical injector 300 may inject the test contrast agent into the object in accordance with the user's injection command. The medical injector 300 may inject physiological saline into the object immediately after the injection of the test contrast agent.

After injection of the test contrast agent, in operation 720, the medical imaging apparatus 100 generates a monitoring image indicating a brightness of the ROI and displays the monitoring image on the user interface 200.

The medical imaging apparatus 100 performs a second scanning (or ROI scanning) on the selected ROI. In particular, when the ROI is selected, the medical imaging apparatus 100 moves the table 190 in the D1 direction and fixes the table 190 when the ROI is located between the X-ray source 110 and the X-ray detector 120 to prepare the second scanning. In addition, when the test contrast agent is injected into the object, X-ray emissions and detections are repeated at predetermined time intervals in a state that the X-ray source 110 and the X-ray detector 120 are fixed. In this aspect, the medical imaging apparatus 100 performs X-ray emissions and detections on the same ROI a plurality of number of times at predetermined time intervals.

The medical imaging apparatus 100 sequentially generates a plurality of X-ray images of the ROI, i.e., a plurality of ROI images with time, in accordance with the second scanning. In addition, the medical imaging apparatus 100 generates a monitoring image to monitor variations in the brightness of the ROI images by creating a graph showing the brightness of the ROI images, and displays the generated monitoring image for user's confirmation.

The medical imaging apparatus 100 detects the peak of the test contrast agent, creates a mark M1 at the peak, and displays the mark M1 on the monitoring image. In particular, the medical imaging apparatus 100 marks the peak of the test contrast agent on the monitoring image.

In operation 730, the medical imaging apparatus 100 receives a confirmation of the peak from the user. The user may confirm whether the mark is correctly located at the peak-occurrence time via the user interface 200.

If the position of the mark M1 corresponds to the peak-occurrence time, the user may finally confirm the mark M1 by touching the mark M1 displayed on the screen with a hand or a finger. The user may also click the mark M1 or press the enter key of the keyboard for final confirmation. If the position of the mark M1 does not correspond to the peak-occurrence time, the user may change the position of the mark M1 by dragging the mark M1 displayed on the screen with a hand or a finger. The user may also use a hardware device, such as a mouse, to change the position of the mark M1 instead of dragging the mark M1 displayed on the screen.

If there is no user's confirmation within a predetermined time period, the medical imaging apparatus 100 may recognize, as a default, that the mark M1 created in operation 730 is formed at a correct position of the peak-occurrence time.

When the position of the mark M1 is finally determined, in operation 740, the medical imaging apparatus 100 calculates a time of scanning the area of the diagnosis, i.e., the starting time of the third scanning, based on the arrival time period of the test contrast agent at the peak and the arrival time period of the contrast agent at the area of diagnosis from the ROI.

The area of the diagnosis may be input by the user before the initiation of the first scanning or before the injection of the contrast agent. However, a time of inputting the area of the diagnosis is not limited thereto, and may be any time before the initiation of the third scanning.

When the position of the mark is finally determined, the medical imaging apparatus 100 determines the arrival time period of the test contrast agent at the peak. In particular, the determined arrival time period of the test contrast agent at the peak may be regarded as the same as the arrival time period of the main contrast agent at the peak.

Meanwhile, the storage unit 450 may store a distance from the ROI to the area of the diagnosis and/or an arrival time period of the contrast agent at the area of the diagnosis from the ROI.

When the distance from the ROI to the area of the diagnosis is stored in the storage unit 450, the medical imaging apparatus 100 may acquire an arrival time period P4 of the contrast agent at the area of the diagnosis from the ROI by using a proportional expression of a distance S1 from an injection site of the contrast agent to the ROI, a distance S2 from the ROI to the area of the diagnosis, and a time period P3 taken for the test (or main) contrast agent to arrive at the peak and may calculate the starting time of the third scanning based on the acquired arrival time period P4 of the contrast agent.

When an arrival time period P5 of the contrast agent at the area of diagnosis from the ROI is stored in the storage unit 450, the medical imaging apparatus 100 may calculate the starting time of the third scanning by using the time period P3 taken for the test (or main) contrast agent to arrive at the peak and the arrival time period P5 of the contrast agent stored in the storage unit 450. In particular, the controller 400 may calculate the starting time of the third scanning as a time after P3+P5 from injection of the main contrast agent.

An arrival time period P6 of the contrast agent at the ROI from the injection site of the contrast agent and the arrival time period P5 of the contrast agent at the area of the diagnosis from the ROI may be stored in the storage unit 450. In this case, the medical imaging apparatus 100 may correct the arrival time period P5 of the contrast agent stored in the storage unit 450 based on a difference between the time period P3 taken for the test (or main) contrast agent to arrive at the peak and determined by the position of the mark and the arrival time period P6 of the contrast agent stored in the storage unit 450, and may calculate the starting time of the third scanning by using the time period P3 and the corrected arrival time period P5. In particular, if the corrected arrival time period P5 is referred to as P7, the medical imaging apparatus 100 may calculate the starting time of the third scanning as a time after P3+P7 from injection of the main contrast agent.

When the starting time of the third scanning is calculated, in operation 750, the medical imaging apparatus 100 injects the main contrast agent into the object via the medical injector 300.

When the user inputs a command to inject the main contrast agent via the user interface 200, the medical injector 300 may inject the main contrast agent into the object in accordance with the user's injection command. Alternatively, the medical injector 300 may inject the main contrast agent into the object at a time after a predetermined time period pre-set for the injection of the main contrast agent, e.g., after 5 seconds, from the peak-occurrence time of the test contrast agent. The medical injector 300 may inject physiological saline into the object immediately after the injection of the main contrast agent.

In addition, operation 750 may be performed before operation 740 in accordance with a user's input or a predetermined setting time.

In operation 760, the medical imaging apparatus 100 generates a diagnostic image by scanning the area of the diagnosis at the calculated starting time of the third scanning and displays the diagnostic image on the user interface 200.

First, the medical imaging apparatus 100 moves the table 190 correspondingly to the area of the diagnosis and controls the X-ray source 110 mounted on the gantry 102 to emit X-rays at predetermined time intervals by rotating the gantry 102 at a predetermined speed.

The medical imaging apparatus 100 generates a plurality of X-ray images of the area of the diagnosis in response to the third scanning, and displays the X-ray images on the user interface 200. In this regard, the generated X-ray images, i.e., diagnostic images, may be 2D projected images of the x-y plane and a 3D image or a 3D stereo image created by combining the 2D projected images.

Meanwhile, before initiating the third scanning, the medical imaging apparatus 100 may output a guidance message "Hold your breath" to the object 30.

As described above, the medical imaging apparatus 100 may accurately calculate the starting time of scanning the area of the diagnosis based on the arrival time period of the test contrast agent at the peak. In this aspect, side effects of the contrast agent may be minimized, and the contrast of the diagnostic image may be maximized by predicting the arrival time period of the main contrast agent at the peak by using a small amount of the contrast agent before injection of the main contrast agent and accurately calculating the starting time of scanning the area of the diagnosis. In addition, the medical imaging apparatus 100 may reduce the artifact of the diagnostic image by outputting a guidance message about breathing based on the calculated starting time of scanning the area of the diagnosis.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. A medical imaging apparatus comprising:
    a scanning mechanism configured to scan an object;
    an image generator circuitry configured to generate a monitoring image to monitor at least one variation in a brightness of a region of interest (ROI) of the object;
    a controller circuitry configured to determine a peak of the brightness in the monitoring image;
    a user interface configured to display the monitoring image and an indicator of the peak; and
    a memory configured to store a second arrival time period during which at least one from among a test contrast agent and a main contrast agent arrives at an area of a diagnosis of the object from the region of interest (ROI) of the object,
    wherein the controller circuitry is further configured to:
        calculate a first arrival time period during which the brightness reaches the peak after an injection of the test contrast agent based on a position of the indicator; and
        calculate a starting time of a scanning of the area of the diagnosis by adding the first arrival time period and the second arrival time period to a time of occurrence of an injection of the main contrast agent.

2. The medical imaging apparatus according to claim 1, wherein the scanning mechanism is further configured to scan the region of interest (ROI) of the object.

3. The medical imaging apparatus according to claim 2, wherein the image generator circuitry is further configured to generate a region of interest (ROI) image based on a result of the scanning the region of interest (ROI) of the object.

4. The medical imaging apparatus according to claim 3, wherein the scanning mechanism is fixed at a peripheral position of the region of interest (ROI) of the object and is further configured to scan the region of interest (ROI) of the object at least twice at predetermined time intervals.

5. The medical imaging apparatus according to claim 3, wherein the scanning mechanism is further configured to scan the area of the diagnosis.

6. The medical imaging apparatus according to claim 5, wherein the area of the diagnosis is different from the region of interest (ROI) of the object.

7. The medical imaging apparatus according to claim 5, wherein the scanning mechanism is further configured to scan the region of interest (ROI) of the object in correspondence with the injection of the test contrast agent and to scan the area of the diagnosis in correspondence with the injection of the main contrast agent.

8. The medical imaging apparatus according to claim 5, wherein the user interface is further configured to receive, from the user, information that indicates at least one from among the region of interest (ROI) of the object and the area of the diagnosis.

9. The medical imaging apparatus according to claim 8, wherein the scanning mechanism is further configured to perform scout scanning on the object that is usable by the image generator circuitry for generating a scout image.

10. The medical imaging apparatus according to claim 9, wherein the user interface is further configured to display the scout image, and the region of interest (ROI) of the object is set on the scout image.

11. The medical imaging apparatus according to claim 5, wherein the scanning mechanism is further configured to scan the area of the diagnosis at least twice at predetermined time intervals while rotating around the area of the diagnosis.

12. The medical imaging apparatus according to claim 5, wherein the image generator circuitry is further configured to generate a diagnostic image in accordance with the scanning the area of the diagnosis, and
    the user interface is further configured to display the diagnostic image.

13. The medical imaging apparatus according to claim 5, further comprising a voice output device configured to output an audio message that includes information relating to instructing the object to hold his or her breath before the scanning the area of the diagnosis is initiated.

14. The medical imaging apparatus according to claim 1, wherein the user interface is further configured to display the indicator on the monitoring image.

15. The medical imaging apparatus according to claim 14, wherein the monitoring image includes an image that shows a graph that depicts at least one variation in the brightness of a region of interest (ROI) image as a function of time.

16. The medical imaging apparatus according to claim 1, wherein the user interface is further configured to receive, from a user, a confirmation of the position of the indicator.

17. The medical imaging apparatus according to claim 16, wherein the user interface is further configured to receive, from the user, a position change command that relates to changing the position of the indicator.

18. The medical imaging apparatus according to claim 17, wherein the user interface is further configured to display the indicator based on a changed position that results from the position change command.

19. A method for controlling a medical imaging apparatus, the method comprising:
   scanning an object;
   generating a monitoring image configured to monitor at least one variation in a brightness in a region of interest (ROI) of the object;
   determining a peak of the brightness in the monitoring image;
   displaying the monitoring image and an indicator of the peak;
   storing a second arrival time period during which at least one from among a test contrast agent and a main contrast agent arrives at an area of a diagnosis of the object from the region of interest (ROI) of the object;
   calculating a first arrival time period during which the brightness reaches the peak after an injection of the test contrast agent based on a position of the indicator; and
   calculating a starting time of a scanning of the area of the diagnosis by adding the first arrival time period and the second arrival time period to a time of occurrence of an injection of the main contrast agent.

20. The method according to claim 19, wherein the scanning the object comprises scanning the region of interest (ROI) of the object.

21. The method according to claim 20, wherein the generating the monitoring image comprises generating a region of interest (ROI) image based on a result of the scanning the region of interest (ROI) of the object, and
   the monitoring image includes an image which is usable for monitoring the at least one variation in the brightness of the region of interest (ROI) image.

22. The method according to claim 21, further comprising scanning the area of the diagnosis.

23. The method according to claim 22, wherein the scanning the region of interest (ROI) of the object comprises scanning the region of interest (ROI) of the object in correspondence with the injection of the test contrast agent, and
   the scanning the area of the diagnosis comprises scanning the area of the diagnosis in correspondence with the injection of the main contrast agent.

24. The method according to claim 22, wherein the scanning the area of the diagnosis of the object comprises outputting, by a voice output device, an audio message that includes information relating to instructing the object to hold his or her breath before the scanning the area of the diagnosis is initiated.

25. The method according to claim 19, further comprising receiving, from a user, a confirmation of the position of the indicator.

* * * * *